US011078165B2

(12) United States Patent
Grüber et al.

(10) Patent No.: US 11,078,165 B2
(45) Date of Patent: Aug. 3, 2021

(54) COMPOUNDS FOR TREATING TUBERCULOSIS

(71) Applicants: NANYANG TECHNOLOGICAL UNIVERSITY, Singapore (SG); NATIONAL UNIVERSITY OF SINGAPORE, Singapore (SG)

(72) Inventors: Gerhard Grüber, Singapore (SG); Roderick Wayland Bates, Singapore (SG); Adam Hotra, Singapore (SG); Thomas Dick, Singapore (SG); Kevin Pethe, Singapore (SG)

(73) Assignees: NANYANG TECHNOLOGICAL UNIVERSITY, Singapore (SG); NATIONAL UNIVERSITY OF SINGAPORE, Singapore (SG)

( * ) Notice: Subject to any disclaimer, the term of this patent is extended or adjusted under 35 U.S.C. 154(b) by 0 days.

(21) Appl. No.: 16/485,973

(22) PCT Filed: Feb. 15, 2018

(86) PCT No.: PCT/SG2018/050075
§ 371 (c)(1),
(2) Date: Aug. 14, 2019

(87) PCT Pub. No.: WO2018/151681
PCT Pub. Date: Aug. 23, 2018

(65) Prior Publication Data

US 2020/0231550 A1 Jul. 23, 2020

(30) Foreign Application Priority Data

Feb. 15, 2017 (SG) ............................ 10201701210T

(51) Int. Cl.

| | |
|---|---|
| ***A61K 31/437*** | (2006.01) |
| ***C07D 239/48*** | (2006.01) |
| ***A61P 31/06*** | (2006.01) |
| ***A61K 31/47*** | (2006.01) |

(52) U.S. Cl.
CPC .......... *C07D 239/48* (2013.01); *A61K 31/437* (2013.01); *A61K 31/47* (2013.01); *A61P 31/06* (2018.01)

(58) Field of Classification Search
CPC .................................................... A61K 31/437
See application file for complete search history.

(56) References Cited

U.S. PATENT DOCUMENTS

2010/0317643 A1 12/2010 Goodacre et al.

FOREIGN PATENT DOCUMENTS

| | | | |
|---|---|---|---|
| RU | 2468013 | C2 | 11/2012 |
| WO | 2005/013996 | A2 | 2/2005 |
| WO | 2014/106762 | A1 | 7/2014 |

OTHER PUBLICATIONS

Written Opinion and ISR in PCT/SG2018/050075.
Compound with Registry No. 923689-76-3. Feb. 28, 2007 [Retrieved on Apr. 20, 2018 from CAS Registry].
Compound with Registry No. 923686-49-1. Feb. 28, 2007 [Retrieved on Apr. 20, 2018 from CAS Registry].
Compound with Registry No. 923226-95-3. Feb. 26, 2007 [Retrieved on Apr. 20, 2018 from CAS Registry].
Compound with Registry No. 923234-54-2. Feb. 26, 2007 [Retrieved on Apr. 20, 2018 from CAS Registry].
Compound with Registry No. 923250-05-9. Feb. 26, 2007 [Retrieved on Apr. 20, 2018 from CAS Registry].
Compound with Registry No. 923179-57-1. Feb. 26, 2007 [Retrieved on Apr. 20, 2018 from CAS Registry].
Compound with Registry No. 923688-56-6. Feb. 28, 2007 [Retrieved on Apr. 20, 2018 from CAS Registry].
Compound with Registry No. 946244-84-4. Sep. 7, 2007 [Retrieved on Apr. 20, 2018 from CAS Registry].
Rilova E, et al., Design Synthesis and Biological Evaluation of 4-Amino-N-(4-aminophenyl)benzamide Analogues of Quinoline-Based SGI-1027 as Inhibitors of DNA Methylation. ChemMedChem, Feb. 13, 2014, vol. 9, No. 3, pp. 590-601 [Retrieved on Apr. 20, 2018] <DOI: 10.1002/CMDC.201300420> Scheme 1.
India Examination Report for Application No. 201917036557.
Russian Search Report for Russian Application No. 2019128534/04(056145).
Russian Office Action dated Jun. 10, 2021 for Russian Application No. 2019128534104(056145).

*Primary Examiner* — Brian E McDowell
(74) *Attorney, Agent, or Firm* — JCIP; Joseph G. Chu; Jeremy I. Maynard

(57) ABSTRACT

The present invention relates to pyrimidine compounds and compositions for treating tuberculosis. These compounds may be used to target the $F_1$ domain of F-ATP synthase and may be used with bedaquiline or 6-chloro-2-ethyl-N-[[4-[4-[4-(trifluoromethoxy)phenyl]piperidin-1-yl]phenyl]methyl] imidazo[1,2-a]pyridine-3-carboxamide (Q203) or a combination thereof.

10 Claims, 9 Drawing Sheets

COMPOUNDS FOR TREATING TUBERCULOSIS

TECHNICAL FIELD OF THE INVENTION

The present invention relates to compounds and compositions for treating tuberculosis.

BACKGROUND OF THE INVENTION

The following discussion of the background to the invention is intended to facilitate understanding of the present invention. However, it should be appreciated that the discussion is not an acknowledgment or admission that any of the material referred to was published, known or a part of the common general knowledge in any jurisdiction as at the priority date of the application.

Tuberculosis (TB) is an infectious disease caused by the bacterium *Mycobacterium tuberculosis*. New therapeutical strategies are needed to combat the tuberculosis pandemic and the spread of multi-drug-resistant (MDR) and extensively drug-resistant (XDR) forms of TB, which remain a serious public health challenge worldwide.

Bedaquiline (BDQ; Sirturo®) is an antitubercular compound that belongs to the chemical class of diarylquinolines. However, despite the clinical success of BDQ, clinical resistance to BDQ has been reported in extensively drug-resistant tuberculosis (XDR-TB) patients.

Thus, there exists a need to develop compounds or a composition thereof for treating TB.

SUMMARY OF THE INVENTION

In a first aspect, there is provided a compound having a structure represented by the following formula:

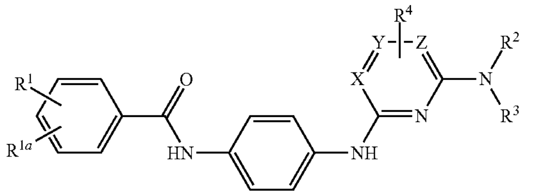

wherein $R^1$ and $R^{1a}$ are independently H, halogen, $C_1$-$C_4$ alkyl, $C_1$-$C_4$ alkoxy, OH;

$R^2$ =H, $C_1$-$C_4$ alkyl, $C_1$-$C_4$ alkyl alcohol, $C_1$-$C_4$alkoxy, —$CH_2COOEt$;

$R^3$ =H, $C_1$-$C_4$ alkyl;

$R^4$ =H, halogen, $C_1$-$C_4$ alkyl, $C_1$-$C_4$ alkoxy;

X, Y and Z are independently C or N.

Advantageously, the compounds of the present invention target the F-ATP synthase. The $F_1F_O$ ATP synthase (F-ATP synthase) is one of the essential enzymes in supplying the energy requirement of both the proliferating aerobic and hypoxic dormant stage of the life cycle of mycobacteria. The enzyme is composed of nine subunits in the stoichiometry of $\alpha_3$:$\beta_3$:γ:δ:ε:a:b:b':$c_9$, and organized in a membrane-embedded $F_O$ domain (a:b:b':$c_9$) and a water soluble $F_1$ part ($\alpha_3$:$\beta_3$:γ:δ:ε). The $F_1$ domain contains three catalytic αβ-pairs that form an $\alpha_3$:$\beta_3$ hexamer, in which ATP synthesis or ATP hydrolysis takes place. This catalytic $\alpha_3$:$\beta_3$-headpiece is linked via the two central stalk subunits γ, ε and the peripheral stalk with the ion-pumping $F_O$ part. The $F_O$ domain contains subunit a, and a ring structure consisting of 9 c subunits. The rotational movement of the c-ring is proposed to trigger the central subunits γ and ε to rotate, causing sequential conformational changes in the nucleotide-binding subunits α and β, followed by the synthesis of ADP+Pi to ATP.

The F-ATP synthase has been shown to be essential for optimal growth in *Mycobacterium smegmatis* and *M. tuberculosis* (Mt), with the latter causing TB. This is different in other prokaryotes and eukaryotes (i.e. humans), where the enzyme is dispensable for growth on fermentable carbon sources and where increased glycolytic flux can compensate for the loss of oxidative phosphorylation. The difference was attributed to be due to an extraordinarily high amount of ATP required to synthesize a mycobacterial cell. The uniqueness of the mycobacterial F-ATP synthase lies also in its incapability of proton-translocation, and its low or latent ATPase activity of the fast- or slow-growing form, respectively.

The clinical success of BDQ, an inhibitor of the $F_1F_O$ ATP synthase, validated this enzyme complex as a vulnerable target for anti-tuberculosis drug development.

Furthermore, F-ATP synthase belongs to the orchestra of enzymes forming the electron transport chain (ETC; FIG. 1), to which the cytochrome c oxidase (cyt-bc1-aa3) and a bacterial specific cytochrome bd-type menaquinol oxidase (cyt-bd) belong to, and the F-ATP synthase contributes to the generation of ATP. The imidazopyridine amide (IPA) compound, Q203, was developed, targeting the cyt-bc1-aa3, and underlined the important role of ETC enzymes as a drug target.

More advantageously, the compounds of the present invention target the soluble $F_1$ part of the mycobacterial $F_1F_O$-ATP synthase in drug resistant MDR and XDR-TB. The concept is anchored in novel insights by the inventors into Nature's paradigms for securing energy inside mycobacteria, new drug targets inside the key catalyst responsible for ATP synthesis and development of new compounds. In addition, the compounds of the present invention were found to contribute to a synergistic efficacy with BDQ and Q203 in a multi-drug combination, thereby addressing the challenges of MDR and XDR-TB. Importantly, the inventors have identified novel targets in the $F_1$ domain and conducted an in silico compound screening exercise based on their structural and biochemical data of the soluble $F_1$ part of the F-ATP synthase, and subsequently identified novel small molecule inhibitors. Without being bound by theory, it is believed that the compounds of the present invention target the soluble $F_1$ part of the F-ATP synthase, while BDQ interacts with the c subunit and the ε subunit at specific amino acid residues, and Q203 targets the cytochrome c oxidase, cyt-bc1-aa3. As such, when used with BDQ and/or Q203, BDQ still binds to the $F_O$ portion and the € subunit of F-ATP synthase and Q203 still binds to cytochrome c oxidase in the presence of the compounds of the present invention.

Preferably, $R^2$ is ethyl and $R^3$ is H. In various embodiments, the presence of a di-substituted alkyl amine moiety on the pyrimidine ring, such as a compound Br DE (Table 1), as well as bigger substituents on $R^2$ resulted in a drop in both inhibitory activities (as reflected by a relatively higher $IC_{50}$ and $MIC_{50}$). In contrast, good inhibitory activities were observed when $R^2$ is ethyl and $R^3$ is H. The most active compounds were when $R^2$ is methyl or ethyl. For instance, comparing Cpd 6 wherein $R^2$ is ethyl and $R^3$ is H, with the compound Br DE wherein $R^2$ is ethyl and $R^3$ is ethyl, significantly lower $IC_{50}$ and $MIC_{50}$ values were achieved with Cpd 6. As such, this shows that a di-substituted alkyl amine moiety on the pyrimidine ring resulted in a drop in both inhibitory activities (as reflected by a relatively higher $IC_{50}$ and $MIC_{50}$).

Preferably, X is N, Y and Z are C.

Preferably, $R^1$ is selected from the group consisting of 3-Br, 3-F, 3-OH, 4-Me and 4-OMe.

Preferably, $R^{1a}$ is selected from the group consisting of 5-Br, 5-F and 5-OH.

Preferably, $R^{1a}$ is hydrogen.

Preferably, $R^2$ is selected from the group consisting of $—CH_2CH_2OH$, $—CH_2COOEt$, methyl, ethyl and isopropyl.

In a second aspect, there is provided a compound of one of the following structures:

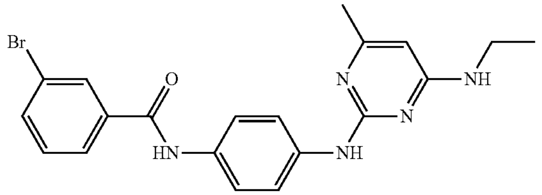

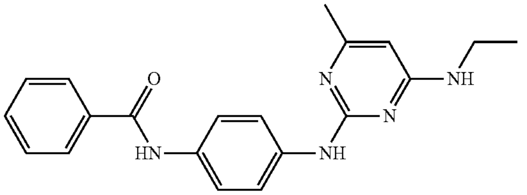

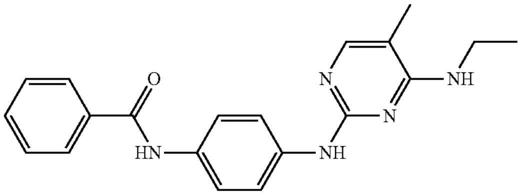

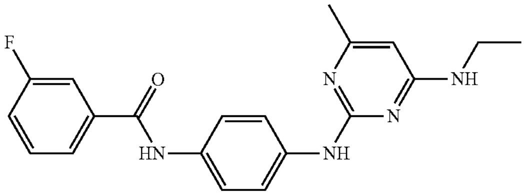

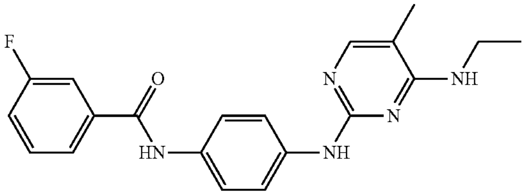

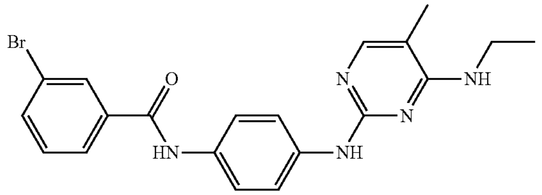

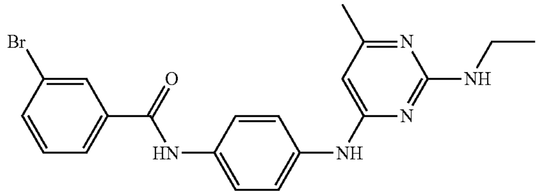

-continued

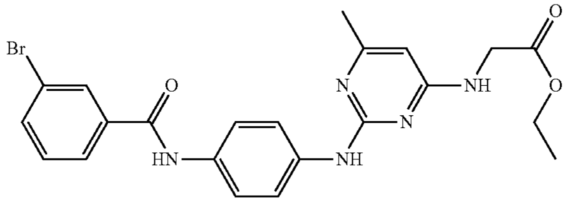

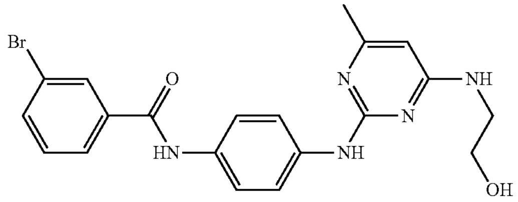

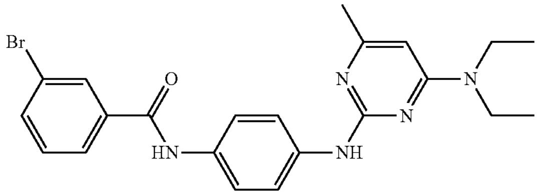

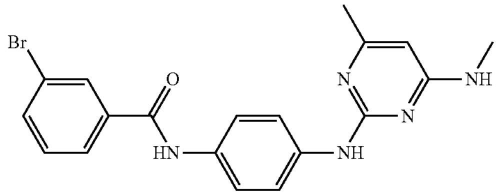

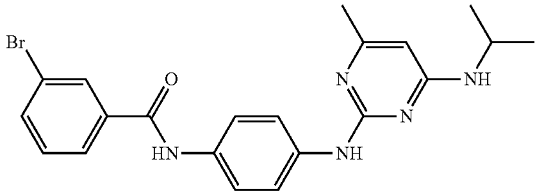

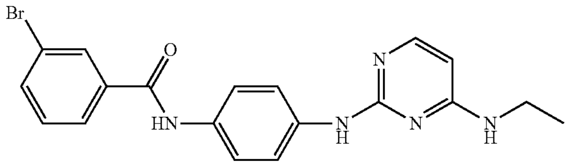

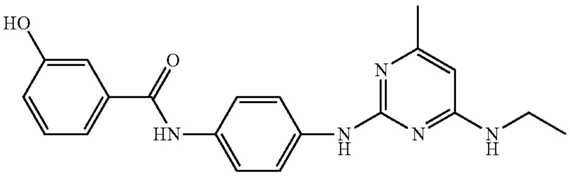

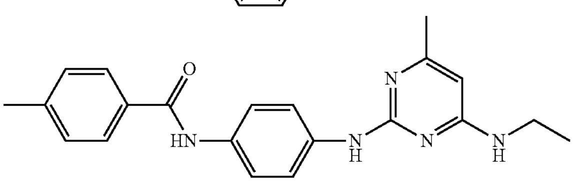

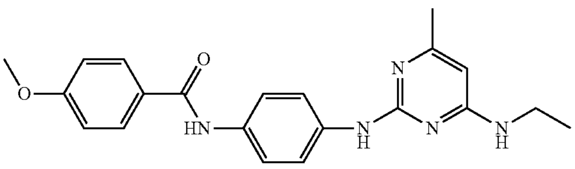

or a pharmaceutically acceptable salt thereof.

In a third aspect, there is provided a composition comprising a compound as described above and bedaquiline or Q203 or a combination thereof. The chemical name of bedaquiline is 1-(6-bromo-2-methoxy-quinolin-3-yl)-4-dimethylamino-2-naphthalen-1-yl-1-phenyl-butan-2-ol. Its molecular formula is $C_{32}H_{31}BrN_2O_2$ and chemical structure is:

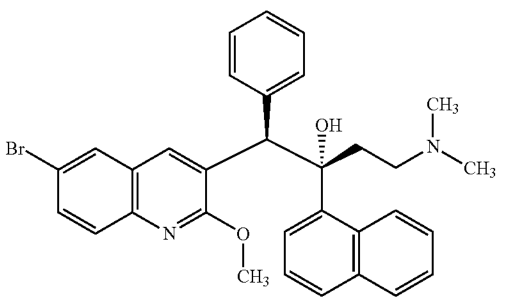 [SMILES: COc1nc2ccc(Br)cc2cc1[C@@H](c1ccccc1)[C@@](O)(CCN(C)C)c1cccc2ccccc12]

The chemical name of Q203 is 6-chloro-2-ethyl-N-[[4-[4-[4-(trifluoromethoxy)phenyl]piperidin-1-yl]phenyl] methyl]imidazo[1,2-a]pyridine-3-carboxamide. Its molecular formula is $C_{29}H_{28}ClF_3N_4O_2$ and chemical structure is:

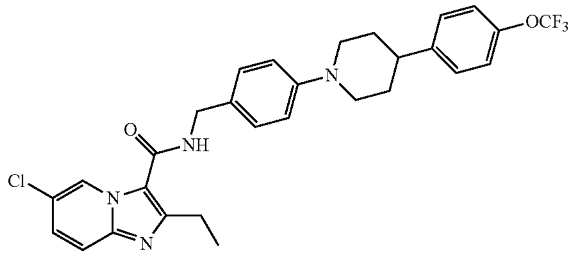 [SMILES: CCc1nc2ccc(Cl)cn2c1C(=O)NCc1ccc(N2CCC(c3ccc(OC(F)(F)F)cc3)CC2)cc1]

In a fourth aspect, there is provided a compound as described above for use in therapy.

In a fifth aspect, there is provided a composition as described above for use in therapy.

In a sixth aspect, there is provided use of a compound as described above in the manufacture of a medicament for treating tuberculosis.

In a seventh aspect, there is provided use of a composition as described above in the manufacture of a medicament for treating tuberculosis.

Preferably, the tuberculosis is multi-drug-resistant tuberculosis or extensively drug-resistant tuberculosis.

In an eighth aspect, there is provided a compound as described above for the treatment of tuberculosis.

In a ninth aspect, there is provided a composition as described above for the treatment of tuberculosis.

In a tenth aspect, there is provided a kit for treating tuberculosis, the kit comprising a compound as described above and bedaquiline or 6-chloro-2-ethyl-N-[[4-[4-[4-(trifluoromethoxy)phenyl]piperidin-1-yl]phenyl]methyl]imidazo[1,2-a]pyridine-3-carboxamide (Q203) or a combination thereof.

In an eleventh aspect, there is provided a method of treating tuberculosis in a patient, wherein the method comprises administering to a patient, a therapeutically effective amount of a compound as described above.

Preferably, the method further comprises adding bedaquiline and/or 6-chloro-2-ethyl-N-[[4-[4-[4-(trifluoromethoxy)phenyl]piperidin-1-yl]phenyl]methyl]imidazo[1,2-a]pyridine-3-carboxamide (Q203).

In a twelfth aspect, there is provided a method of synthesizing a compound as described above, the method comprising the step of: (a) coupling a first compound with a second compound in the presence of a first base.

Preferably, the first base is selected from the group consisting of triethylamine, N,N-diethylisopropylamine, N,N-diisopropylethylamine (DIPEA), tripropylamine and trioctylamine.

Preferably, the method further comprises step (b) synthesizing the first compound by mixing an amine or an amine salt with 2,4-dichloro-6-methylpyrimidine in the presence of the first base to form the first compound.

Preferably, the method further comprises step (c) synthesizing the second compound, and wherein step (c) comprises hydrogenating a N-(4-nitrophenyl)benzamide or a derivative thereof to form a N-(4-aminophenyl)benzamide or a derivative thereof.

Preferably, step (c) further comprises step (d) adding oxalyl chloride, 4-nitroaniline and a catalytic amount of dimethylformamide in the presence of a second base to a benzoic acid derivative to form the N-(4-nitrophenyl)benzamide or the derivative thereof.

Preferably, the second base is selected from the group consisting of potassium carbonate, sodium carbonate, potassium bicarbonate, sodium bicarbonate, lithium hydroxide, potassium hydroxide and sodium hydroxide.

BRIEF DESCRIPTION OF THE DRAWINGS

The invention will now be described, by way of example only, with reference to the accompanying drawings, in which.

DETAILED DESCRIPTION

Figure 1:
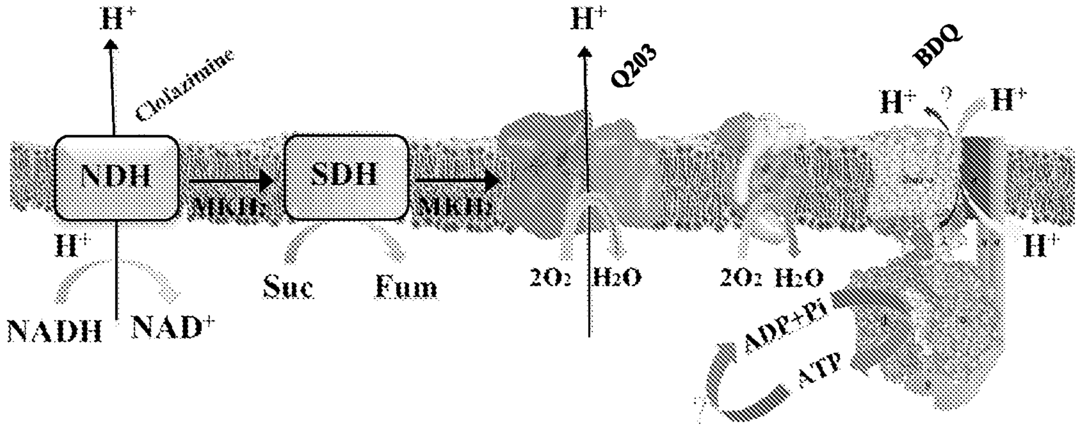
FIG. 1 illustrates the oxidative phosphorylation pathway in Mt with the compound Q203 and BDQ targeting the cyt-bc1-aa3 and F-ATP synthase.

Particular embodiments of the present invention will now be described with reference to the accompanying drawings. The terminology used herein is for the purpose of describing particular embodiments only and is not intended to limit the scope of the present invention. Additionally, unless defined otherwise, all technical and scientific terms used herein have the same meanings as commonly understood by one or ordinary skill in the art to which the present invention belongs. Where possible, the same reference numerals are used throughout the figures for clarity and consistency.

Throughout the specification, unless otherwise indicated to the contrary, the terms "comprising", "consisting of", and the like, are to be construed as non-exhaustive, or in other words, as meaning "including, but not limited to".

Throughout the specification, unless the context requires otherwise, the word "comprise" or variations such as "comprises" or "comprising", will be understood to imply the inclusion of a stated integer or group of integers but not the exclusion of any other integer or group of integers.

Throughout the specification, unless the context requires otherwise, the word "include" or variations such as "includes" or "including", will be understood to imply the inclusion of a stated integer or group of integers but not the exclusion of any other integer or group of integers.

As used herein, the term "about" typically means +/−5% of the stated value, more typically +/−4% of the stated value, more typically +/−3% of the stated value, more typically +/−2% of the stated value, even more typically +/−1% of the stated value, and even more typically +/−0.5% of the stated value.

As used herein, the term "pharmaceutically acceptable salt" refers to a salt prepared from a pharmaceutically acceptable non-toxic base or acid.

As used herein, the term "treatment", "treat" and "therapy", and synonyms thereof refer to both therapeutic treatment and prophylactic or preventative measures, wherein the object is to prevent or slow down (lessen) TB. Those in need of such treatment include those already with a TB infection as well as those prone to getting it or those in whom a TB infection is to be prevented.

As used herein, the term "therapeutically effective amount" of a compound will be an amount of active agent that is capable of preventing or at least slowing down (lessening) TB. Dosages and administration of compounds, compositions and formulations of the present invention may be determined by one of ordinary skill in the art of clinical pharmacology or pharmacokinetics. See, for example, Mordenti and Rescigno, (1992) Pharmaceutical Research. 9:17-25; Morenti et al., (1991) Pharmaceutical Research. 8:1351-1359; and Mordenti and Chappell, "The use of interspecies scaling in toxicokinetics" in Toxicokinetics and New Drug Development, Yacobi et al. (eds) (Pergamon Press: NY, 1989), pp. 42-96. An effective amount of the compounds, compositions and formulations of the present invention to be employed therapeutically will depend, for example, upon the therapeutic objectives, the route of administration, and the condition of the patient. As used in the specification herein, the term "patient" includes humans and animals. Accordingly, it will be necessary for the therapist to titer the dosage and modify the route of administration as required to obtain the optimal therapeutic effect. A typical daily dosage might range from about 1 μg/kg/day to about 50 mg/kg/day of the patient's body weight or more per day, about 1 mg/kg/day to about 50 mg/kg/day, about 1 mg/kg/day to about 10 mg/kg/day, preferably about 1 μg/kg/day to about 10 mg/kg/day.

As used herein, the term "alkyl" is a branched or unbranched saturated hydrocarbon group of 1 to 10 carbon atoms, such as methyl, ethyl, w-propyl, isopropyl, w-butyl, isobutyl, s-butyl, i-butyl, w-pentyl, isopentyl, s-pentyl, neopentyl, hexyl, heptyl, octyl, nonyl, decyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from 1 to 6 (e.g., from 1 to 4) carbon atoms. In a preferred embodiment, the term "alkyl" is a branched or unbranched saturated hydrocarbon group of 1 to 4 carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups. The term "alkylamino" specifically refers to an alkyl group that is substituted with one or more amino groups. The term "azaalkyl" specifically refers to an alkyl group wherein at least one carbon is replaced by a nitrogen. The term "oxaalkyl" specifically refers to an alkyl group wherein at least one carbon is replaced by an oxygen.

As used herein, the terms "alkoxy" and "alkoxyl" as used herein to refer to an alkyl or cycloalkyl group bonded through an ether linkage; that is, an "alkoxy" group can be defined as—$OA^1$ where $A^1$ is alkyl or cycloalkyl as defined above. "Alkoxy" also includes oligomers of alkoxy groups as just described; that is, an alkoxy can be a polyether such as —$OA^1$—$OA^2$ or —$OA^1$—$(OA^2)_a$—$OA^3$, where "a" is an integer of from 1 to 200 and $A^1$, $A^2$, and $A^3$ are alkyl and/or cycloalkyl groups.

As used herein, the term "haloheterocycle" refers to a cyclic compound that has atoms of at least two different elements as members of its ring(s), and wherein the cyclic compound bears a halogen atom as a substituent. The halogen may be fluorine, chlorine, bromine or iodine. An example of a haloheterocycle is a chloroheterocycle. For instance, 2-chloro-N-ethyl-5-methylpyrimidin-4-amine and PY6 are chloroheterocycles. Even though a haloheterocycle such as a chloroheterocycle is used herein, it would be appreciated that other halogens such as bromine, fluoro or iodine, such that a bromoheterocycle, fluoroheterocycle or iodoheterocycle may be used in GP4.

As used herein, the term "derivative" or "analog" refers to a compound that has a similar or related structure as a compound that the term is used in reference to.

Throughout this disclosure, certain embodiments may be disclosed in a range format. It should be understood that the description in range format is merely for convenience and brevity and should not be construed as a limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. Ranges are not limited to integers, and can include decimal measurements. This applies regardless of the breadth of the range.

Other aspects of the invention will become apparent to those of ordinary skill in the art upon review of the following description of specific embodiments of the invention in conjunction with the accompanying figures.

In an aspect of the present invention, there is provided a compound having a structure represented by the following formula:

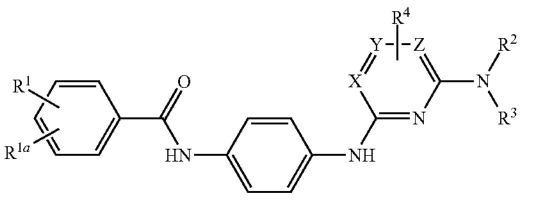

wherein $R^1$ and $R^{1a}$ are independently H, halogen, $C_1$-$C_4$ alkyl, $C_1$-$C_4$ alkoxy, OH;

$R^2$=H, $C_1$-$C_4$ alkyl, $C_1$-$C_4$ alkyl alcohol, $C_1$-$C_4$ alkoxy, —$CH_2COOEt$;

$R^3$=H, $C_1$-$C_4$ alkyl;

$R^4$=H, halogen, $C_1$-$C_4$ alkyl, $C_1$-$C_4$alkoxy;

X, Y and Z are independently C or N.

Advantageously, the compounds of the present invention target the F-ATP synthase. The $F_1F_O$ ATP synthase (F-ATP synthase) is one of the essential enzymes in supplying the energy requirement of both the proliferating aerobic and hypoxic dormant stage of the life cycle of mycobacteria. The enzyme is composed of nine subunits in the stoichiometry of $\alpha_3$:$\beta_3$:γ:δ:ε:a:b:b':$c_9$, and organized in a membrane-embedded $F_O$ domain (a:b:b':$c_9$) and a water soluble $F_1$ part ($\alpha_3$:$\beta_3$:γ:δ:ε). The $F_1$ domain contains three catalytic αβ-pairs that form an $\alpha_3$:$\beta_3$ hexamer, in which ATP synthesis or ATP hydrolysis takes place. This catalytic $\alpha_3$:$\beta_3$-headpiece is linked via the two central stalk subunits γ, ε and the peripheral stalk with the ion-pumping $F_O$ part. The $F_O$ domain contains subunit a, b and b' as well as a ring structure consisting of 9 c subunits. The rotational movement of the c-ring is proposed to trigger the central subunits γ and ε to rotate, causing sequential conformational changes in the nucleotide-binding subunits α and β, followed by the synthesis of ADP+Pi to ATP.

The F-ATP synthase has been shown to be essential for optimal growth in *Mycobacterium smegmatis* and *M. tuberculosis* (Mt), with the latter causing TB. This is different in other prokaryotes and eukaryotes (i.e. humans), where the enzyme is dispensable for growth on fermentable carbon sources and where increased glycolytic flux can compensate for the loss of oxidative phosphorylation. The difference was attributed to be due to an extraordinarily high amount of ATP required to synthesize a mycobacterial cell. The uniqueness of the mycobacterial F-ATP synthase lies also in its incapability of proton-translocation, and its low or latent ATPase activity of the fast- or slow-growing form, respectively.

The clinical success of BDQ, an inhibitor of the $F_1F_O$ ATP synthase, validated this enzyme complex as a vulnerable target for anti-tuberculosis drug development.

Furthermore, F-ATP synthase belongs to the orchestra of enzymes forming the electron transport chain (ETC; FIG. 1), to which the cytochrome c oxidase (cyt-bc1-aa3) and a bacterial specific cytochrome bd-type menaquinol oxidase (cyt-bd) belong to, and the F-ATP synthase contributes to the generation of ATP. The imidazopyridine amide (IPA) compound, Q203, was developed, targeting the cyt-bc1-aa3, and underlined the important role of ETC enzymes as a drug target.

More advantageously, the compounds of the present invention target the soluble $F_1$ part of the mycobacterial $F_1F_O$-ATP synthase in drug resistant MDR and XDR-TB. The concept is anchored in novel insights by the inventors into Nature's paradigms for securing energy inside mycobacteria, new drug targets inside the key catalyst responsible for ATP synthesis and development of new compounds. In addition, the compounds of the present invention were found to contribute to a synergistic efficacy with BDQ and Q203 in a multi-drug combination, thereby addressing the challenges of MDR and XDR-TB. Importantly, the inventors have identified novel targets in the $F_1$ domain and conducted an in silico compound screening exercise based on their structural and biochemical data of the soluble $F_1$ part of the F-ATP synthase, and subsequently identified novel small molecule inhibitors. Without being bound by theory, it is believed that the compounds of the present invention target the soluble $F_1$ part of the F-ATP synthase, while BDQ interacts with the c subunit and the ε subunit at specific amino acid residues, and Q203 targets the cytochrome c oxidase, cyt-bc1-aa3. As such, when used with BDQ and/or Q203, BDQ still binds to the $F_O$ portion and the ε subunit of F-ATP synthase and Q203 still binds to cytochrome c oxidase in the presence of the compounds of the present invention.

Advantageously, the compounds of the present invention do not bear resemblance to any compounds that are currently used for treating tuberculosis.

In various embodiments, $R^2$ is ethyl and $R^3$ is H. The presence of a di-substituted alkyl amine moiety on the pyrimidine ring, such as a compound Br DE (Table 1), as well as bigger substituents on $R^2$ resulted in a drop in both inhibitory activities (as reflected by a relatively higher $IC_{50}$ and $MIC_{50}$). As such, when $R^2$ comprises a longer carbon chain such as $C_5$ and greater, poorer inhibitory activities were observed. The inventors found that the most active compounds were when $R^2$ is methyl or ethyl. Advantageously, good inhibitory activities were observed when $R^2$ is ethyl and $R^3$ is H. For instance, comparing Cpd 6 wherein $R^2$ is ethyl and $R^3$ is H, with the compound Br DE wherein $R^2$ is ethyl and $R^3$ is ethyl, significantly lower $IC_{50}$ and $MIC_{50}$ values were achieved with Cpd 6. As such, this shows that a di-substituted alkyl amine moiety on the pyrimidine ring resulted in a drop in both inhibitory activities (as reflected by a relatively higher $IC_{50}$ and $MIC_{50}$).

In various embodiments, X is N, Y and Z are C.

In various embodiments, $R^1$ is selected from the group consisting of 3-Br, 3-F, 3-OH, 4-Me and 4-OMe.

In various embodiments, $R^{1a}$ is selected from the group consisting of 5-Br, 5-F and 5-OH.

In various embodiments, $R^{1a}$ is hydrogen.

In various embodiments, $R^2$ is selected from the group consisting of $-CH_2CH_2OH$, $-CH_2COOEt$, methyl, ethyl and isopropyl.

In another aspect of the present invention, there is provided a compound of one of the following structures:

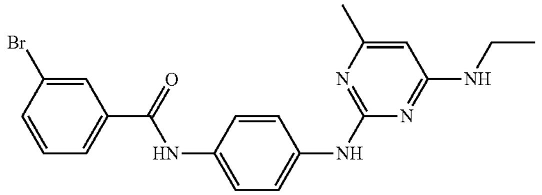

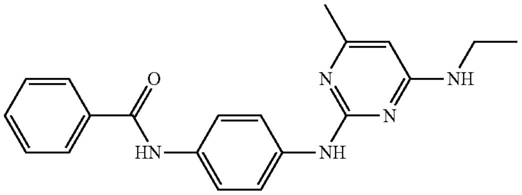

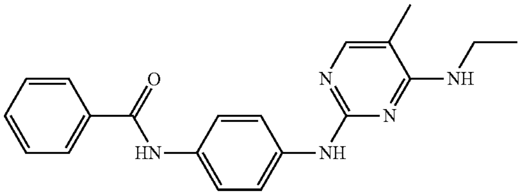

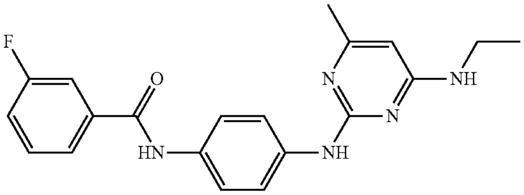

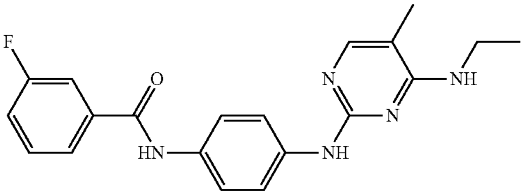

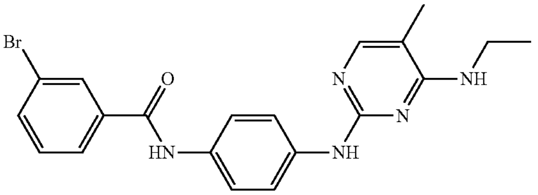

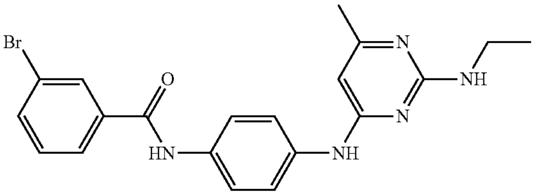

-continued

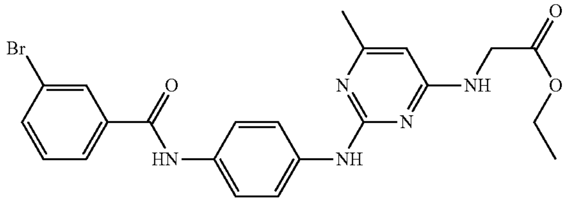

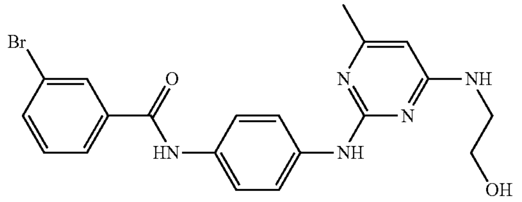

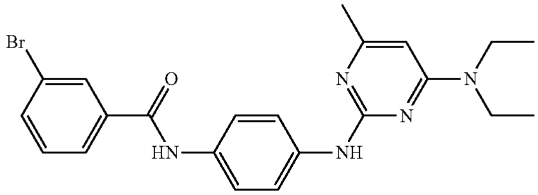

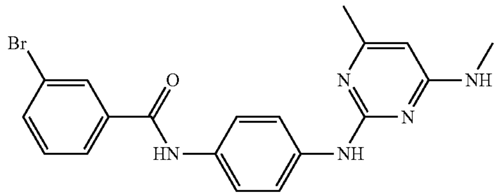

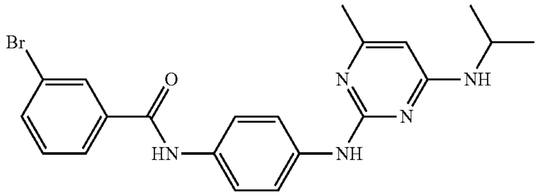

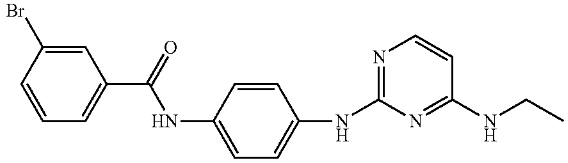

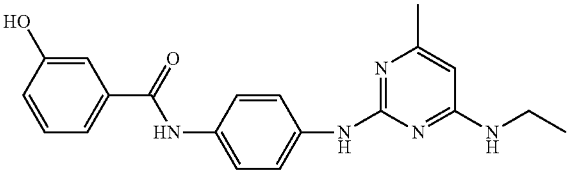

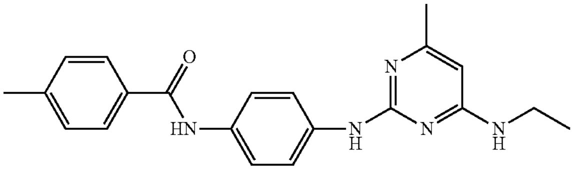

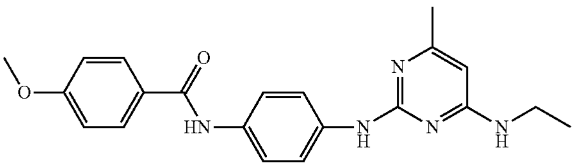

or a pharmaceutically acceptable salt thereof.

Figure 6A:
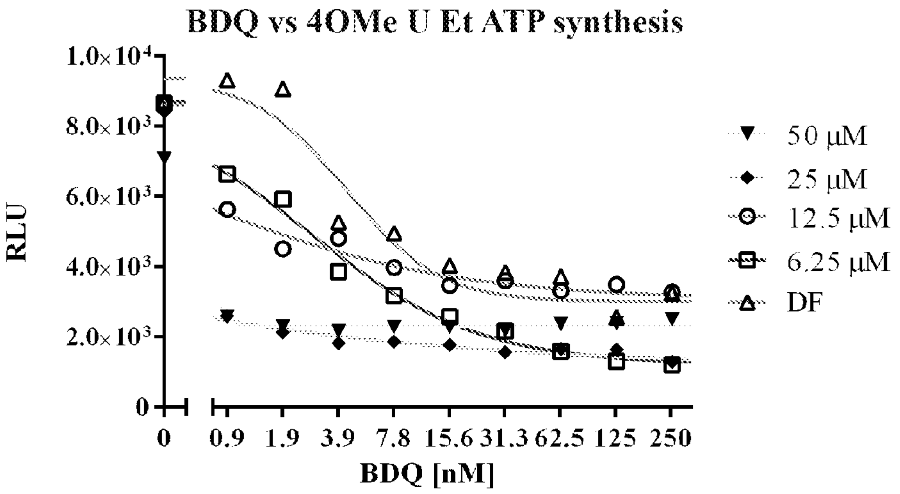
FIGS. 6A and 6B show that the effect of whole cell ATP synthesis inhibition in *M. bovis* BCG by BDQ is significantly increased when combined with the cpd 6 analogs, N-(4-((4-(ethylamino)-6-methylpyrimidin-2-yl)amino)phenyl)-4-methoxybenzamide (4OMe U Et) (FIG. 6A) or 3-bromo-N-(4-((4-(diethylamino)-6-methylpyrimidin-2-yl) amino)phenyl)benzamide (Br DE) (FIG. 6B).
Figure 6B:
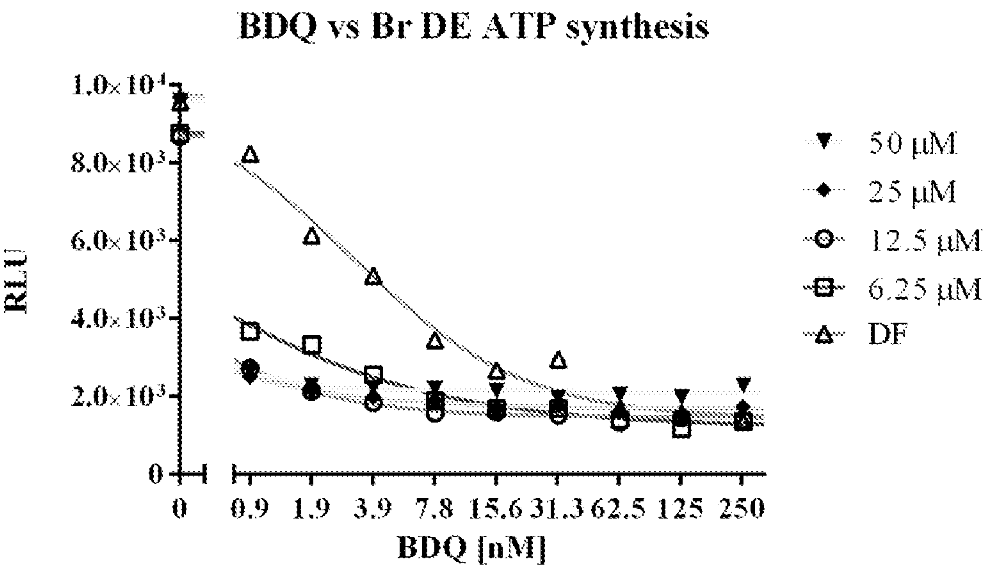

In another aspect of the present invention, there is provided a composition comprising a compound as described above and bedaquiline or Q203 or a combination thereof. For instance, the combination of BDQ with a cpd 6 analog, N-(4-((4-(ethylamino)-6-methylpyrimidin-2-yl)amino)phenyl)-4-methoxybenzamide (4OMe U Et) (FIG. 6A) or 3-bromo-N-(4-((4-(diethylamino)-6-methylpyrimidin-2-yl)amino)phenyl)benzamide (Br DE) (FIG. 6B), resulted in increased whole cell ATP synthesis inhibition in *M. bovis* BCG. Compared to the control wherein no drug was used (DF=drug free), there was a significant increase in the inhibition of the whole cell ATP synthesis in *M. bovis* BCG when 4OMe U Et or Br DE was used, as evidenced by the decrease in ATP synthesis (FIG. 6A and 6B). Furthermore, the combination of BDQ at 12.5 nm, Q203 at 0.5 nM and cpd6 at 12.5 μM effectively inhibited the whole cell ATP synthesis in *M. bovis* BCG. Compared to the control wherein no drug was used, there was at least a two-fold increase in the inhibition of the whole cell ATP synthesis in *M. bovis* BCG, as evidenced by the at least two-fold decrease in ATP synthesis. Advantageously, these concentrations are below the $IC_{50}$ values of the individual compounds.

In another aspect of the present invention, a compound as described above or a composition as described above is suitable for use in therapy.

In another aspect of the present invention, there is provided use of a compound as described above in the manufacture of a medicament for treating tuberculosis.

In another aspect of the present invention, there is provided use of a composition as described above in the manufacture of a medicament for treating tuberculosis.

Preferably, the tuberculosis is multi-drug-resistant tuberculosis or extensively drug-resistant tuberculosis.

In another aspect of the present invention, there is provided a compound as described above for the treatment of tuberculosis.

In another aspect of the present invention, there is provided a composition as described above for the treatment of tuberculosis.

In another aspect of the present invention, there is provided a kit for treating tuberculosis, the kit comprising a compound as described above and BDQ or Q203 or a combination thereof.

In another aspect of the present invention, there is provided a method of treating tuberculosis in a patient, wherein the method comprises administering to a patient, a therapeutically effective amount of a compound as described above.

Preferably, the method further comprises adding BDQ and/or Q203.

In another aspect of the present invention, there is provided a method of synthesizing a compound as described above, the method comprising the step of: (a) coupling a first compound with a second compound in the presence of a first base. In various embodiments, the first compound is a chloroheterocycle and the second compound is a N-(4-aminophenyl)benzamide or a derivative thereof.

In various embodiments, the first base is a tertiary amine. Preferably, the first base is selected from the group consisting of triethylamine, N,N-diethylisopropylamine, N,N-diisopropylethylamine (DIPEA), tripropylamine and trioctylamine.

Preferably, the method further comprises step (b) synthesizing the first compound by mixing an amine or an amine salt with 2,4-dichloro-6-methylpyrimidine in the presence of the first base to form the first compound.

Preferably, the method further comprises step (c) synthesizing the second compound, and wherein step (c) comprises hydrogenating a N-(4-nitrophenyl)benzamide or a derivative thereof to form a N-(4-aminophenyl)benzamide or a derivative thereof.

Preferably, step (c) further comprises step (d) adding oxalyl chloride, 4-nitroaniline and a catalytic amount of dimethylformamide in the presence of a second base to a benzoic acid derivative to form the N-(4-nitrophenyl)benzamide or the derivative thereof.

In various embodiments, the second base is an alkali metal salt such as an alkali metal carbonate, an alkali metal bicarbonate or an alkali metal hydroxide. Preferably, the second base is selected from the group consisting of potassium carbonate, sodium carbonate, potassium bicarbonate, sodium bicarbonate, lithium hydroxide, potassium hydroxide and sodium hydroxide.

EXAMPLES

Materials and Methods

Preparation of Inverted Membrane Vesicles from *M. smegmatis*

*M. smegmatis* was selected as the surrogate model for *M. tuberculosis* because there are several advantages to work with it. *M. smegmatis* is a saprophytic and unlike *M. tuberculosis*, it is not pathogenic and can be safely handled under Biosafety level 2 (BSL2) conditions without Biosafety level 3 (BSL3) requirement. In addition, *M. smegmatis* grows much faster (generation time: approximately 3 hours) compared to that of *M. tuberculosis* (generation time: approximately 24 hours). Furthermore, it requires almost 3 to 4 weeks for *M. tuberculosis* to produce colonies on an agar plate, whereas only 2 to 3 days is required for *M. smegmatis* to produce colonies on an agar plate, thereby reducing the duration of experiments. Importantly, *M. smegmatis* IMVs show a detectable ATP hydrolysis activity, which is essential for enzymatic assays to be used or performed.

In order to purify IMVs *of M. smegmatis* for ATP synthesis and—hydrolysis assays, cells were grown overnight at 37° C. in 7H9 supplemented with 10% ADC, 0.5% glycerol and 0.05% Tween80 until they reached an $OD_{600}$ value of 0.4. The culture was expanded in 200 ml supplemented 7H9 and grown in a roller bottle (2 rpm) until $OD_{600}$=0.4. This culture was used to inoculate a 5 l culture that was grown overnight in roller bottles until an $OD_{600}$=0.4. About 5 g (wet weight) of *M. smegmatis* were resuspended in 20 ml membrane preparation buffer (50 mM MOPS, 2 mM $MgCl_2$ pH 7.5) containing EDTA-free protease inhibitor cocktail (1 tablet in 20 ml buffer, Roche-USA) and 1.2 mg/ml lysozyme. The suspension was stirred at room temperature for 45 min and additionally supplemented with 300 μl 1 M $MgCl_2$ and 50 μl DNase I (Thermo Fischer, USA), and continued stirring for another 15 min at room temperature. All subsequent steps were performed on ice. Cells were broken by three passages through an ice precooled Model M-110L Microfluidizer processor (M-110L) at 18,000 psi. The suspension containing lysed cells was centrifuged at 4,200×g at 4° C. for 20 min. The supernatant containing membrane fraction was further subjected to ultracentrifugation 45,000×g at 4° C. for 1 h. The supernatant was discarded and the precipitated membrane fraction was resuspended in membrane preparation buffer containing 15% glycerol, aliquoted, snap frozen and stored at −80° C. The concentrations of the proteins in the vesicles were determined by the BCA method. Inverted membrane vesicles were stored at −80° C.

ATP Synthesis Assay

ATP synthesis was measured in flat bottom white microliter 96 well plates (Corning USA). The reaction mix, made in assay buffer (50 mM MOPS, pH 7.5, 10 mM $MgCl_2$) containing 10 μM ADP, 250 μM Pi and 1 mM NADH. Concentration of Pi was adjusted by addition of 100 mM $KH_2PO_4$ salt dissolved in the assay buffer. ATP synthesis was started by adding inverted vesicles of *M. smegmatis* to a final protein concentration of 5 μg/ml. The reaction mix was incubated at room temperature for 30 min before 50 μl of the CellTiter-glow reagent was added and the mix was incubated for another 10 min in dark at room temperature. Produced luminescence, which is correlated to the synthesized ATP, was measured by a Tecan plate reader Infinite 200 Pro (Tecan USA), using the following parameter: luminescence, integration time 500 ms, attenuation none.

Antimycobacterial Activity

The test compounds and the control drugs were screened against *M. smegmatis* $mc^2$ 155, *M. tuberculosis* H37Rv and *M. bovis* BCG. Initial stock solutions of the test compounds were made in 90% DMSO to a concentration of 10 mM. Ciprofloxacin was used as a positive control and the vehicle DMSO was used as negative control. In the first approach, the compounds were tested on microbial cultures at a fixed concentration of 50 μM. Each of the above strains were cultured at 37° C. in Middlebrook 7H9 broth supplemented with 0.2% glycerol and 10% ADC (Albumin Dextrose Catalase) until logarithmic growth was achieved ($OD_{600}$ 0.4-0.6). The test inoculum was obtained by diluting the suspensions to $OD_{600}$ 0.1 to a final volume of 1 ml in the test tubes and were incubated at 37° C. for 24 hours. Test compounds, which showed no visible growth of bacilli in comparison with the positive and negative controls, were selected as hits.

General Procedure for Synthesis of 2-chloro-pyrimidin-4-amines (GP1)

The corresponding amine or amine hydrochloride and of 2,4-dichloro-6-methylpyrimidine (5.0 g, 30.7 mmol) with 2 equivalents (eq) diisopropylethylamine were stirred for 24 h in ethanol at 50° C. The solvent was evaporated and the isomers were separated by column chromatography using hexane:EtOAc=8:2. The correct isomer was identified by nuclear Overhauser effect spectroscopy (NOESY).

General Procedure for Synthesis of N-(4-nitrophenyl)benzamides (GP2)

To the corresponding benzoic acid (2 g) in dichloromethane (25 ml) was added dropwise oxalyl chloride (1.5 ml, 1.2 eq) in the presence of a catalytic amount of dimethylformamide. The mixture was stirred at room temperature (RT) for 1 h and then concentrated. 4-Nitroaniline (1 eq) and $K_2CO_3$ (2 eq) were added to the obtained material in THF (40 ml) and stirred for 16 hours at RT. The product was filtered and washed with water and hexane.

General Procedure for Hydrogenation of N-(4-nitrophenyl) benzamides (GP3)

The corresponding N-(4-nitrophenyl)benzamide (0.5-2 g) with palladium on carbon (10% wt) in 20 ml of ethyl acetate was hydrogenated under 50 psi of $H_2$ and stirred at RT for 3 h. The flask was depressurised, the reaction mixture was filtered through Celite, and the solvent was evaporated to obtain the product.

General Procedure for Synthesis of N-(4-((4-aminopyrimidin-2-yl)amino)phenyl)-benzamides (GP4)

The corresponding N-(4-aminophenyl)benzamide (200 mg-2 g) and a chloroheterocycle (1 eq) with N,N-Diisopropylethylamine (1 eq) was heated at reflux in dioxane (4-20 ml) for 2-5 days. The precipitate from the reaction mixture was filtered and the product was obtained.

Characterization of Compounds 2,4-dichloro-6-methylpyrimidine (PY1)

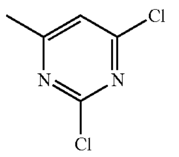

6-Methyluracyl (5 g, 39.65 mmol) was added to phosphoryl chloride (7 eq, 25 ml) and the mixture was heated at reflux for 3 h. The mixture was poured onto ice and the organic layer was extracted by chloroform (3 times, 20 ml) and dried over anhydrous $MgSO_4$. The solvents were evaporated to give the dichloride as yellow crystals (3.77 g, 58%). $^1H$ NMR (400 MHz, $CDCl_3$) δ 7.19 (s, 1H), 2.55 (s, 3H); $^{13}C$ NMR (100 MHz, $CDCl_3$) δ 171.8, 162.4, 160.4, 119.5, 23.8. The $^1H$ NMR spectrum was in accordance with literature: Wang, H., K. Wen, L. Wang, Y. Xiang, X. Xu, Y. Shen and Z. Sun (2012). *Molecules*. 2012, 17(4), 4533-4544.

2,4-dichloro-5-methylpyrimidine (PY2)

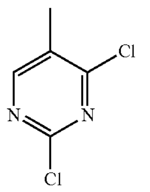

6-Methyluracyl (1 g, 7.93 mmol) was added to phosphoryl chloride (7 eq, 5 ml) and the mixture was heated at reflux for 3 h. The mixture was poured onto ice and the organic layer was extracted with chloroform (3 times, 20 ml) and dried over anhydrous $MgSO_4$. The solvents were evaporated to give the dichloride as yellow crystals (0.62 g, 48%). $^1H$ NMR (400 MHz, $CDCl_3$) δ 8.35 (s, 1H), 2.39(s, 3H); $^{13}C$ NMR (100 MHz, $CDCl_3$) δ 162.5, 160.0, 158.2, 129.1, 15.8. The $^1H$ NMR spectrum was in accordance with literature: Wang, H., K. Wen, L. Wang, Y. Xiang, X. Xu, Y. Shen and Z. Sun (2012). *Molecules*. 2012, 17(4), 4533-4544.

(2-chloro-5-methyl-pyrimidin-4-yl)-ethylamine (PY3)

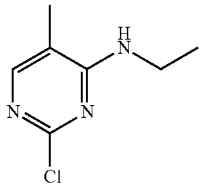

The product was prepared according to the GP1 with ethylamine hydrochloride (500 mg, 6.13 mmol) and 2,4-dichloro-6-methylpyrimidine (1.0 g, 6.13 mmol). The product (575 mg, 56%) was obtained as white crystals. $^1H$ NMR (400 MHz, $CDCl_3$) δ 7.80 (s, 1H), 4.69 (s, 1H), 3.56 (qd, J=7.2, 5.5 Hz, 2H), 2.00 (s, 3H), 1.27 (t, J=7.3 Hz, 3H); $^{13}C$ NMR (100 MHz, $CDCl_3$) δ 162.2, 158.8, 154.6, 111.7, 36.1, 14.7, 13.0; MS ($ESI^+$) 172 ($^{35}Cl$ $M^+$+$H^+$, 100), 174 ($^{37}Cl$ $M^+$+$H^+$, 37); HRMS calculated for $C_7H_{11}N_3Cl$ ($M^+$+$H^+$) 172.0642; found 172.0638 (−2.3 PPM); FTIR (nujol, $cm^{-1}$) $\nu_{max}$ 1244, 1097, 665; 58-63° C.

2-chloranyl-N-ethyl-6-methyl-pyrimidin-4-amine (PY4)

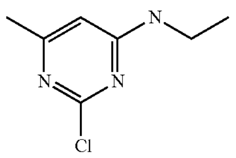

The product was prepared according to the GP1 with ethylamine hydrochloride (2.5 g, 30.67 mmol) and 2,4-dichloro-6-methylpyrimidine (5.0 g, 30.67 mmol). The desired isomer was obtained as yellow crystals (1.74 g, 33%). $^1H$ NMR (400 MHz, $CDCl_3$) δ 6.07 (s, 1H), 5.10 (br, 1H), 3.33 (br, 2H), 2.33 (s, 3H), 1.30-1.21 (m, 3H); $^{13}C$ NMR (100 MHz, $CDCl_3$) δ 166.7, 162.2, 160.2, 99.3, 42.4, 23.9, 12.6; MS ($ESI^+$) m/z 172 (35Cl $M^+$+$H^+$, 100), 174 ($^{37}$ $M^+$+$H^+$, 31); HRMS calculated for $C_7H_{11}N_3{}^{35}Cl$ ($M^+$+$H^+$) 172.0642; found 172.0649 (4.1 PPM); FTIR (nujol, $cm^{-1}$) $\nu_{max}$ 3250, 1600, 968; mp: 74° C. mp: 74-75° C.

4-chloro-N-ethyl-6-methylpyrimidin-2-amine (PY5)

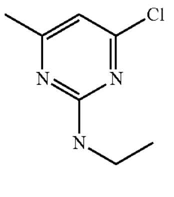

Yield (0.74 g, 14%)

2-chloro-N,N-diethyl-6-methylpyrimidin-4-amine (PY6)

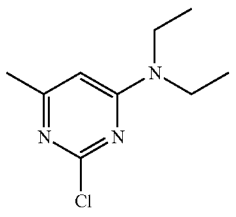

The product was prepared according to the GP1 with diethylamine (244 mg, 3.07 mmol) and 2,4-dichloro-6-methylpyrimidine (500 mg, 3.07 mmol). The desired isomer was obtained as a yellow oil (25 mg, 4%). $^1H$ NMR (400 MHz, $CDCl_3$) δ 6.32 (s, 1H), 3.57 (q, 4H), 2.27 (s, 3H), 1.16 (t, J=7.1 Hz, 6H). $^{13}C$ NMR (100 MHz, $CDCl_3$) δ 168.9, 161.0, 160.7, 107.2, 41.8, 24, 13.03 (1.92); MS ($ESI^+$) m/z 200 ($^{35}Cl$ $M^+$+$H^+$, 100), 202 ($^{37}Cl$ $M^+$+$H^+$, 55); HRMS calculated for $C_9H_{15}N_3{}^{35}Cl$ ($M^+$+$H^+$) 200.0955; found 200.0965 (5.0 PPM); FTIR (neat, $cm^{-1}$) $\nu_{max}$ 3427, 1589, 1047, 445.

4-chloro-N,N-diethyl-6-methylpyrimidin-2-amine (PY7)

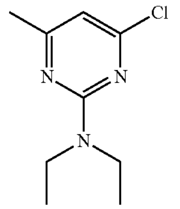

Yield 65%. $^1H$ NMR (400 MHz, $CDCl_3$) δ 6.11 (s, 1H), 3.49 (s, 4H), 2.32 (s, 3H), 1.19 (t, J=7.1 Hz, 6H).

ethyl (2-chloro-6-methylpyrimidin-4-yl)glycinate (PY8)

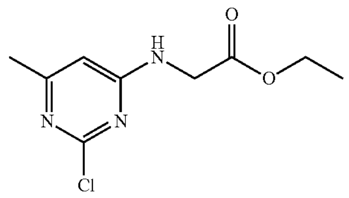

The product was prepared according to the GP1 with glycine ethyl ester hydrochloride (244 mg, 3.07 mmol) and 2,4-dichloro-6-methylpyrimidine (500 mg, 3.07 mmol) (hexane:EtOAc=1:1). Minor 2-substituted isomer was identified by x-ray crystallography. Product was obtained as yellow crystals. The desired isomer was obtained as colourless crystals (338 mg, 48%). $^1H$ NMR (396 MHz, $CDCl_3$) δ 6.50 (s, 1H), 5.59 (br, 1H), 4.22 (q, J=7.1 Hz, 2H), 4.18 (d, J=5.5 Hz, 1H), 2.30 (s, 3H), 1.28 (t, J=7.1 Hz, 3H); $^{13}C$ NMR (100 MHz, $CDCl_3$) δ 163.4, 160.3, 61.8, 42.9, 23.6, 14.2; FTIR (nujol, $cm^{-1}$) $\nu_{max}$ 3250, 1732, 1622, 543; mp: 83-84° C.

ethyl (4-chloro-6-methylpyrimidin-2-yl)glycinate (PY9)

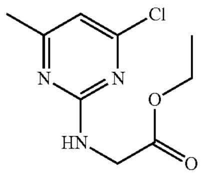

Yield 18%. $^1H$ NMR (396 MHz, $CDCl_3$) δ 6.17 (s, 1H), 5.42 (s, 1H), 4.26 (q, J=7.1 Hz, 2H), 4.16 (s, 2H), 2.34 (s, 3H), 1.31 (t, J=7.2 Hz, 3H).

2-chloro-N-isopropyl-6-methylpyrimidin-4-amine (PY10)

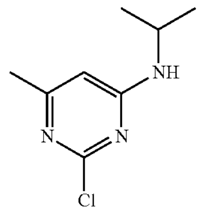

The product was prepared according to the GP1 with isopropylamine (1.09 g, 1.58 ml, 18.40 mmol) and 2,4-dichloro-pyrimidine (3.0 g, 18.40 mmol). The desired isomer was obtained as a yellow oil (1.81 mg, 53%). $^1$H NMR (400 MHz, $CDCl_3$) δ 6.05 (s, 1H), 4.99 (br, 1H), 3.92 (br, 1H), 2.32 (d, J=7.0 Hz, 3H), 1.24 (t, J=6.3 Hz, 6H); $^{13}$C NMR (100 MHz, $CDCl_3$) δ 163.2, 160.3, 43.1, 23.7, 22.5; MS (ESI$^+$) m/z 186 ($^{35}$Cl $M^+$+$H^+$, 100), 188 ($^{37}$Cl $M^+$+$H^+$, 51); HRMS calculated for $C_8H_{13}N_3{}^{35}Cl$ ($M^+$+$H^+$) 186.0798; found 186.0794 (−2.1 PPM); FTIR (neat, $cm^{-1}$) $\nu_{max}$ 3263, 1600, 968.

4-chloro-N-isopropyl-6-methylpyrimidin-2-amine (PY11)

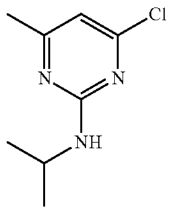

Yield 46%. $^1$H NMR (400 MHz, $CDCl_3$) δ 6.42 (s, 1H), 5.06 (s, 1H), 2.56 (s, 3H), 2.30 (s, 3H), 1.22 (d, J=6.4 Hz, 6H).

2-((2-chloro-6-methylpyrimidin-4-yl)amino)ethan-1-ol (PY12)

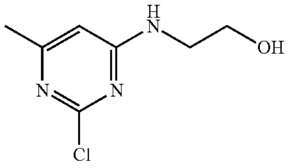

The product was prepared according to the GP1 with ethanolamine (374 mg, 6.13 mmol) and 2,4-dichloro-6-methylpyrimidine (1.0 g, 6.13 mmol). The desired isomer was obtained as white crystals (311 mg, 27%). $^1$H NMR (400 MHz, $CDCl_3$) δ 6.16 (s, 1H), 5.43 (br, 1H), 3.87 (dd, J=9.9, 4.9 Hz, 2H), 3.58 (br, 2H), 2.36 (s, 3H); $^{13}$C NMR (100 MHz, $CDCl_3$) δ 169.6, 162.5, 161.3, 109.6, 77.4, 77.1, 76.7, 44.4, 23.8; MS (ESI$^+$) m/z 188 ($^{35}$Cl $M^+$+$H^+$, 100), 190 ($^{37}$Cl $M^+$+$H^+$, 30); HRMS calculated for $C_7H_{10}N_3{}^{35}ClO$ ($M^+$+$H^+$) 188.0591; found 1588.0599 (4.3 PPM); FTIR (nujol, $cm^{-1}$) $\nu_{max}$ 3251, 1614, 1041, 765; mp: 127-128° C.

2-((4-chloro-6-methylpyrimidin-2-yl)amino)ethan-1-ol (PY13)

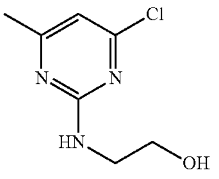

Yield 51%. $^1$H NMR (400 MHz, $CDCl_3$) δ 6.49 (s, 1H), 5.59 (s, 1H), 3.82 (dd, J=9.6, 4.8 Hz, 2H), 3.60 (dd, J=9.9, 5.6 Hz, 2H), 2.32 (s, 3H).

2-chloro-N,6-dimethylpyrimidin-4-amine (PY14)

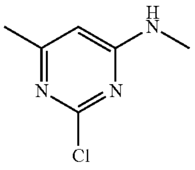

The product was prepared according to the GP1 with methylamine (414 mg, 6.13 mmol) and 2,4-dichloro-6-methylpyrimidine (1.0 g, 6.13 mmol). The desired isomer was obtained as white crystals (415 mg, 43%). $^1$H NMR (400 MHz, $CDCl_3$) δ 6.09 (s, 1H), 5.05 (br, 1H), 2.95 (d, J=5.0 Hz, 3H), 2.35 (s, 3H); $^{13}$C NMR (100 MHz, $CDCl_3$) δ 168.1, 165.0, 159.8, 98.4, 28.5, 23.9; MS (ESI$^+$) m/z 158 ($^{35}$Cl $M^+$+$H^+$, 100), 160 ($^{37}$Cl $M^+$+$H^+$, 34); HRMS calcd for $C_6H_9N_3{}^{35}Cl$ ($M^+$+$H^+$) 158.0485; found 158.0483 (−1.3 PPM); FTIR (nujol, $cm^{-1}$) $\nu_{max}$ 3257, 1614, 972, 835; mp: 134-135° C.

4-chloro-N,6-dimethylpyrimidin-2-amine (PY15)

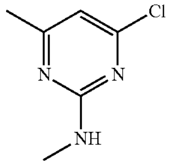

Yield 30%. $^1$H NMR (400 MHz, $CDCl_3$) δ 6.45 (s, 1H), 5.12 (br, 1H), 3.03-2.97 (m, 3H), 2.31 (s, 3H).

2-chloro-N-ethylpyrimidin-4-amine (PY16)

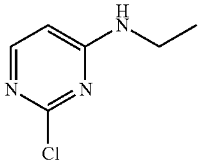

The product was prepared according to the GP1 with ethylamine hydrochloride (414 mg, 5.08 mmol) and 2,4-dichloropyrimidine (756 mg, 5.08 mmol). Product (332 mg, 63%) was obtained as white crystals. $^1$H NMR (400 MHz, $CDCl_3$) δ 8.00 (s, 1H), 6.25 (d, J=6.0 Hz, 1H), 5.50 (br, 1H), 3.36 (br, 2H), 1.25 (t, J=7.2 Hz, 3H); $^{13}$C NMR (100 MHz $CDCl_3$) δ 163.7, 160.2, 155.3, 105.5, 35.3, 14.5; MS (ESI$^+$) m/z 158 ($^{35}$Cl $M^+$+$H^+$, 100), 160 ($^{37}$Cl $M^+$+$H^+$, 55); HRMS calculated for $C_6H_9N_3{}^{35}Cl$ ($M^+$+$H^+$) 158.0485; found 158.0489 (2.5 PPM); FTIR (neat, $cm^{-1}$) $\nu_{max}$ 3417, 1660, 149; mp: 44-45° C.

4-chloro-N-ethylpyrimidin-2-amine (PY17)

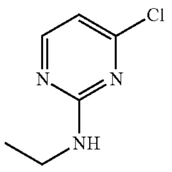

Yield 17% (89 mg)

3-bromo-N-(4-nitrophenyl)benzamide (BA1)

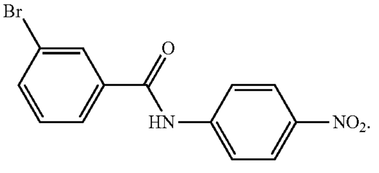 [SMILES: O=C(Nc1ccc([N+](=O)[O-])cc1)c1cccc(Br)c1]

The product was prepared according to the GP2 with 3-bromobenzoic acid (8.77 g, 43.63 mmol) in dichloromethane (25 ml). 4-Nitroaniline (6.0 g, 43.63 mmol) and $K_2CO_3$ (12.0 g, 2 eq). Product was obtained as a yellow solid (13.74 g, 98%). $^1$H NMR (400 MHz, DMSO-$d_6$) δ 10.84 (s, 1H), 8.24 (d, J=9.3 Hz, 2H), 8.14 (s, J=1.8 Hz, 1H), 8.02 (d, J=9.3 Hz, 2H), 7.94 (d, J=7.9 Hz, 1H), 7.81 (d, J=8.9 Hz, 1H), 7.50 (t, J=7.9 Hz, 1H); $^{13}$C NMR (100 MHz, DMSO-$d_6$) δ 165.6, 147.6, 142.5, 137.7, 134.9, 131.1, 127.7, 125.2, 122.1, 120.8. FTIR (nujol, $cm^{-1}$) $v_{max}$ 1685, 1400, 800, 750, 596; Mp: 191-195° C.

N-(4-aminophenyl)-3-bromobenzamide (BA2)

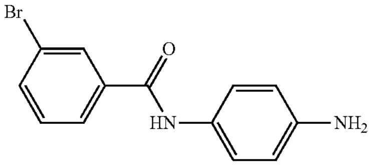

3-Bromo-N-(4-nitrophenyl)benzamide (BA1) (2.5 g, 7.79 mmol) was hydrogenated in 25 ml of EtOAc with sulfur poisoned platinum on carbon (10% wt), for two days under 100 psi of $H_2$ at 100° C. The reaction mixture was filtered through Celite and solvent was evaporated under the reduced pressure. The product was obtained as a grey solid (yield 99%). $^1$H NMR (400 MHz, DMSO-$d_6$) δ 9.97 (s, 1H), 8.10 (s, 1H), 7.92 (d, J=7.8, 0.9 Hz, 1H), 7.75 (d, 1H), 7.47 (dd, J=7.9 Hz, 1H), 7.36 (d, J=8.7 Hz, 2H), 6.61-6.43 (m, 2H), 4.95 (s, 2H). 13C NMR (100 MHz, DMSO-$d_6$) δ 163.5, 145.9, 138.0, 134.3, 131.0, 130.5, 128.2, 127.1, 122.7, 122.1, 114.1; FTIR (nujol, $cm^{-1}$) $v_{max}$ 1643, 1262, 821; MS ($ESI^+$) m/z 291 ($^{79}$Br $M^+$+$H^+$, 100), 293 ($^{81}$Br $M^+$+$H^+$, 94); HRMS calculated for $C_{13}H_{12}{}^{79}BrN_2O$ ($M^+$+$H^+$) 291.0133; found 291.0133 (2.1 PPM); mp: 145-146° C.

N-(4-nitrophenyl)benzamide (BA3)

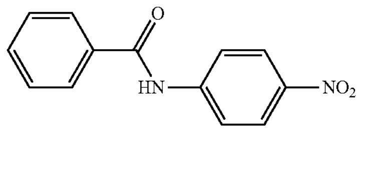 [SMILES: O=C(Nc1ccc([N+](=O)[O-])cc1)c1ccccc1]

The product was prepared according to the GP2 from benzoyl chloride (1.1 g, 1.21 ml, 7.6 mmol) and 4-Nitroaniline (1.0 g, 7.2 mmol). Product was obtained as a yellow solid (886 mg, 48%). $^1$H NMR (400 MHz, DMSO-$d_6$) δ 10.81 (s, 1H), 8.28 (d, J=9.2 Hz, 2H), 8.07 (d, J=9.3 Hz, 2H), 7.98 (d, J=7.0 Hz, 2H), 7.65 (t, J=7.3 Hz, 1H), 7.57 (t, J=7.4 Hz, 2H) ; $^{13}$C NMR (100 MHz, DMSO-$d_6$) δ 166.8, 146.2, 142.9, 134.8, 132.6, 129.0, 128.4, 125.3, 120.3. The $^1$H NMR spectrum was in accordance with literature: Panda, N., R. Mothkuri and D. K. Nayak. *European Journal of Organic Chemistry,* 2014(8): 1602-1605.

N-(4-aminophenyl)benzamide (BA4)

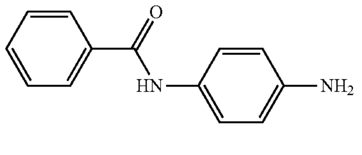

N-(4-Nitrophenyl)benzamide (BA3) (886 mg) was hydrogenated according to the GP3. The product (765 mg, 99%) was obtained as grey solid. $^1$H NMR (400 MHz, DMSO-$d_6$) δ 9.87 (s, 1H), 7.92 (d, J=7.0 Hz, 2H), 7.62-7.44 (m, 3H), 7.38 (d, J=8.7 Hz, 2H), 6.56 (d, J=8.7 Hz, 2H), 4.92 (s, 2H); $^{13}$C NMR (100 MHz, DMSO-$d_6$) δ 165.2, 145.7, 135.8, 131.6, 128.8 (2C), 128.6, 127.9 (2C), 122.7 (2C), 114.2 (2C)3. The $^1$H NMR spectrum was in accordance with literature: Wang, J., X. Yin, J. Wu, D. Wu and Y. Pan. *Tetrahedron,* 2013, 69(48): 10463-10469.

3-fluoro-N-(4-nitrophenyl)benzamide (BA5)

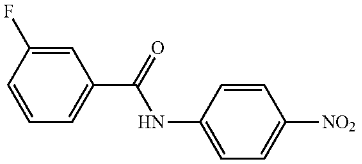

The product was prepared according to the GP2 from 3-florobenzoic acid (1.0 g, 7.14 mmol), para-nitroaniline (1.0 g, 7.2 mmol). The product was obtained as a yellow solid (1.37 g, 69%), $^1$H NMR (396 MHz, DMSO-$d_6$) δ 10.86 (s, 1H), 8.24 (d, J=9.2 Hz, 2H), 8.01 (d, J=9.3 Hz, 2H), 7.85 (d, J=7.8 Hz, 1H), 7.81 (d, 1H), 7.60 (td, J=8.0, 6.0 Hz, 1H), 7.46 (td, J=8.4, 2.2 Hz, 1H); $^{13}$C NMR (100 MHz, DMSO-$d_6$) δ 165.88, 163.65, 161.19, 148.33, 146.28, 142.40, 138.07, 131.08, 125.28, 124.73, 120.87, 119.23, 119.02, 115.41, 115.18; FTIR (nujol, $cm^{-1}$) $v_{max}$ 1610, 1344, 1193, 752; mp: 175° C. mp: 174-175° C.

N-(4-aminophenyl)-3-fluorobenzamide (BA6)

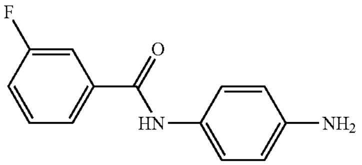 [SMILES: O=C(Nc1ccc([N+](=O)[O-])cc1)c1cccc(F)c1]

3-Fluoro-N-(4-nitrophenyl)benzamide (BA5) (857 mg, 3.29 mmol) was hydrogenated according to the GP3. The product was obtained as a grey solid (754 mg, 99%). $^1$H NMR (396 MHz, DMSO-$d_6$) δ 9.93 (s, 1H), 7.78 (d, J=7.8

Hz, 1H), 7.72 (d, J=9.9 Hz, 1H), 7.55 (td, J=8.0, 6.0 Hz, 1H), 7.45-7.38 (m, 1H), 7.36 (d, J=8.7 Hz, 2H), 6.55 (d, J=8.8 Hz, 2H), 4.95 (s, 2H); $^{13}$C NMR (100 MHz, DMSO-$d_6$) δ 163.74, 163.71, 163.68, 161.25, 145.95, 138.21, 138.15, 131.01, 130.93, 128.28, 124.16, 124.13, 122.81, 118.61, 118.40, 115.96, 114.86, 114.64, 114.18. FTIR (nujol, $cm^{-1}$) $\nu_{max}$ 1847, 1587, 1519, 1462, 1377, 1317, 1244, 1199, 1097, 1014, 898, 815, 750, 653, 520, 478; mp: 113° C. mp: 112-114° C.

4-methyl-N-(4-nitrophenyl)benzamide (BA7)

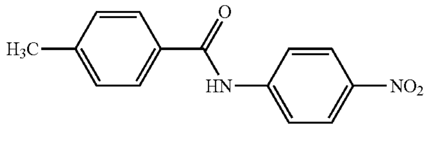 [SMILES: Cc1ccc(C(=O)Nc2ccc([N+](=O)[O-])cc2)cc1]

The product was prepared according to the GP2 from 4-methylbenzoic acid (2 g, 14.69 mmol) and para-nitroaniline (2.0 g, 14.49 mmol). The product was obtained as a yellow solid (2.52 g, 67%). $^1$H NMR (396 MHz, DMSO-$d_6$) δ 10.71 (s, 1H), 8.26 (d, J=9.2 Hz, 2H), 8.07 (d, J=9.3 Hz, 2H), 7.90 (d, J=8.2 Hz, 2H), 7.37 (d, J=8.1 Hz, 2H), 2.40 (s, 3H); $^{13}$C NMR (100 MHz, DMSO-$d_6$) δ 166.5, 146.1, 142.9, 131.8, 129.5, 128.5, 125.3, 120.3, 21.5; MS ($ESI^+$) m/z 257 ($M^+$+$H^+$); HRMS calculated for $C_{14}H_{13}N_2O_3$ ($M^+$+$H^+$) 257.0926; found 257.0945 (7.4 PPM); FTIR (nujol, $cm^{-1}$) $\nu_{max}$ 1672, 1336, 1178, 1109, 848; mp: 205° C.

N-(4-aminophenyl)-4-methylbenzamide (BA8)

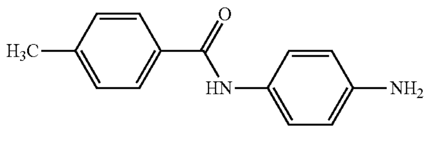 [SMILES: Cc1ccc(C(=O)Nc2ccc(N)cc2)cc1]

4-Methyl-N-(4-nitrophenyl)benzamide (BA7) (2 g, 6.66 mmol) was hydrogenated according to GP3. The product was obtained as a yellow solid (1.44 g, 98%). $^1$H NMR (400 MHz, DMSO-$d_6$) δ 9.77 (s, 1H), 7.83 (d, J=8.1 Hz, 2H), 7.36 (d, J=8.7 Hz, 2H), 7.30 (d, J=8.0 Hz, 1H), 6.54 (d, J=8.7 Hz, 1H), 4.91 (s, 2H), 2.37 (s, 3H); $^{13}$C NMR (100 MHz, DMSO-$d_6$) δ 164.9, 145.6, 141.4, 132.8, 129.3, 128.6, 127.9, 122.7, 114.1, 21.5; MS ($ESI^+$) m/z 227 ($M^+$+$H^+$); HRMS calculated for $C_{14}H_{15}N_2O$ ($M^+$+$H^+$) 227.1184; found 227.1190 (2.6 PPM); FTIR (nujol, $cm^{-1}$) $\nu_{max}$ 1639, 1612, 1327, 833; mp: 141-144° C.

4-methoxy-N-(4-nitrophenyl)benzamide (BA9)

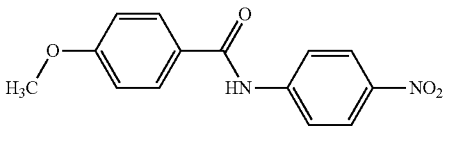 [SMILES: COc1ccc(C(=O)Nc2ccc([N+](=O)[O-])cc2)cc1]

The product was prepared according to the GP2 from 4-methoxybenzoic acid (2 g, 13.15 mmol) and p-nitroaniline (1.81 g 13.13 mmol). The product was obtained as a yellow solid (2.76 g, 77%). $^1$H NMR (400 MHz, DMSO-$d_6$) δ 10.64 (s, 1H), 8.25 (d, J=9.2 Hz, 1H), 8.06 (d, J=9.2 Hz, 1H), 7.99 (d, J=8.8 Hz, 1H), 7.09 (d, J=8.9 Hz, 1H), 3.85 (s, 3H); $^{13}$C NMR (100 MHz, DMSO-$d_6$) δ 166.0, 162.9, 146.3, 142.7, 130.5, 126.9, 126.6, 125.3, 120.2, 114.3, 112.9, 56.0; MS ($ESI^+$) m/z 273 ($M^+$+$H^+$); HRMS calculated for $C_{14}H_{13}N_2O_4$ ($M^+$+$H^+$) 273.0875; found 257.0905 (11.0 PPM); FTIR (nujol, $cm^{-1}$), $\nu_{max}$ 1651, 1184, 848, 455; mp: 173-175° C.

N-(4-aminophenyl)-4-methoxybenzamide (BA10)

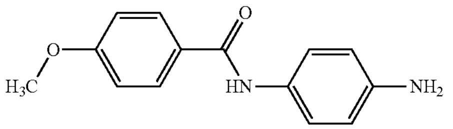

4-Methoxy-N-(4-nitrophenyl)benzamide (BA9) (1 g, 3.67 mmol) was hydrogenated according to GP3. The product was obtained as a grey solid (870 mg, 98%). BA10 was reported in EP 2 505 198 A1. $^1$H NMR (400 MHz, DMSO-$d_6$) δ 9.71 (s, 1H), 7.91 (d, J=8.7 Hz, 2H), 7.35 (d, J=8.7 Hz, 2H), 7.03 (d, J=8.8 Hz, 2H), 6.53 (d, J=8.7 Hz, 2H), 4.89 (s, 2H), 3.83 (s, 3H); $^{13}$C NMR (100 MHz, DMSO-$d_6$) δ 164.6, 162.0, 145.5, 129.7, 128.7, 127.9, 122.8, 114.1, 113.9, 55.9.

3-acetoxybenzoic acid (BA11)

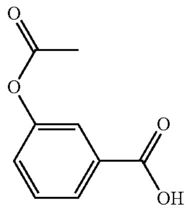

Acetic anhydride (10 ml, 105.79 mmol) was added drop-wise to a cooled solution of 3-hydroxybenzoic acid (2 g, 14.48 mmol) in pyridine (20 ml), and the mixture was stirred at RT overnight. The mixture was cooled, poured onto ice and extracted with diethyl ether (50 ml). The product was obtained as a colourless solid (2.29 g, 88%). $^1$H NMR (400 MHz, DMSO-$d_6$) δ 8.58 (s, J=4.1 Hz, 1H), 7.83 (d, J=7.9 Hz, 2H), 7.66 (s, J=2.0 Hz, 2H), 7.55 (t, J=7.9 Hz, 2H), 7.39 (d, J=6.7 Hz, 3H), 2.29 (s, J=1.9 Hz, 6H) ; $^{13}$C NMR (100 MHz, DMSO-$d_6$) δ 169.7, 167.0, 151.0, 132.7, 130.3, 127.1, 126.9, 123.1, 21.34. The $^1$H NMR and $^{13}$C NMR spectra were in accordance with literature: Kesenheimer, C., A. Kalogerakis, A. Meissner and U. Groth. *Chemistry,* 2010, 16(29): 8805-8821.

3-((4-nitrophenyl)carbamoyl)phenyl acetate (BA12)

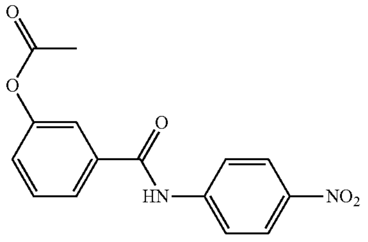 [SMILES: CC(=O)Oc1cccc(C(=O)Nc2ccc([N+](=O)[O-])cc2)c1]

The product was prepared according to the GP2 from 3-acetoxybenzoic acid (2.29 g, 12.71 mmol) and 4-nitroaniline (1.75 g 12.69 mmol). The product was obtained as colourless solid (3.41 g, 90%). $^1$H NMR (400 MHz, DMSO-$d_6$) δ 10.86 (s, 1H), 8.28 (d, J=9.3 Hz, 2H), 8.07 (d, J=9.3 Hz, 2H), 7.90 (d, J=7.9 Hz, 1H), 7.75 (s, 1H), 7.62 (t, J=7.9

Hz, 1H), 7.42 (d, J=5.9 Hz, 1H), 2.32 (s, 3H); $^{13}C$ NMR (100 MHz, DMSO-$d_6$) δ 169.7, 165.7, 150.9, 145.8, 143.1, 136.1, 130.2, 126.3, 125.9, 125.3, 121.8, 120.4, 21.3; FTIR (nujol, $cm^{-1}$) $\nu_{max}$ 3562, 1730, 1674, 752; mp: 173° C.

3-((4-aminophenyl)carbamoyl)phenyl acetate (BA13)

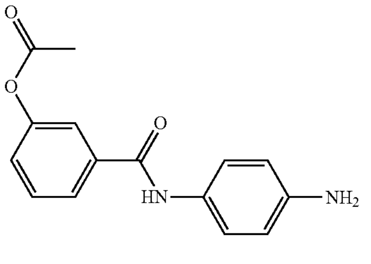 [SMILES: CC(=O)Oc1cccc(C(=O)Nc2ccc(N)cc2)c1]

3-((4-Nitrophenyl)carbamoyl)phenyl acetate (BA12) (2 g, 6.66 mmol) was hydrogenated according to GP3. The product was obtained as a yellow solid (1.44 g, 5.33 mmol), yield 80%. $^1H$ NMR (400 MHz, DMSO-$d_6$) δ 9.94 (s, 1H), 7.85 (d, J=7.9 Hz, 1H), 7.69 (s, 1H), 7.55 (t, J=7.9 Hz, 1H), 7.39 (d, J=8.7 Hz, 1H), 7.33 (d, J=8.1 Hz, 1H), 6.57 (d, J=8.7 Hz, 1H), 4.93 (s, 2H), 2.31 (s, 1H); $^{13}C$ NMR (100 MHz, DMSO-$d_6$) δ 169.7, 164.0, 150.9, 145.8, 137.2, 129.9, 128.4, 125.3, 125.2, 122.8, 122.6, 121.4, 114.2, 21.2, 14.5. FTIR (nujol, $cm^{-1}$) $\nu_{max}$ 1737, 1651, 823; mp: 231-233° C.

N-(4-aminophenyl)-3-hydroxybenzamide (BA14)

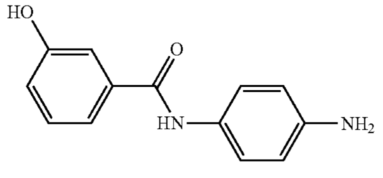 [SMILES: Nc1ccc(NC(=O)c2cccc(O)c2)cc1]

3-((4-Nitrophenyl)carbamoyl)phenyl acetate (BA12) (635 mg, 2.35 mmol) was dissolved in 30 ml of ethanol and cooled to 0° C. After addition of 15 ml 2 M NaOH the solution was stirred for 1 h, glacial acetic acid was added until the pH was <7, the solvents were evaporated and the product was obtained as a yellow solid (491 mg, 92%). $^1H$ NMR (396 MHz, DMSO-$d_6$) δ 9.77 (s, 1H), 9.67 (s, 1H), 7.46-7.18 (m, 5H), 6.93 (d, J=7.8 Hz, 1H), 6.54 (d, J=6.9 Hz, 2H), 4.92 (s, 1H); $^{13}C$ NMR (100 MHz, DMSO-$d_6$) δ 165.2, 157.8, 145.6, 137.3, 129.8, 128.7, 122.6, 118.5, 118.4, 114.9, 114.15. The $^1H$ NMR and $^{13}C$ NMR spectra were in accordance with literature: Tran, A. T., D. Wen, N. P. West, E. N. Baker, W. J. Britton and R. J. Payne. *Org Biomol Chem,* 2013 11(46): 8113-8126.

3-bromo-N-(4-((4-(ethylamino)-5-methylpyrimidin-2-yl)amino)phenyl)benzamide (Br T Et)

N-(4-Aminophenyl)-3-bromobenzamide (BA2) (85 mg, 291 μmol) and 2-chloro-N-ethyl-5-methylpyrimidin-4-amine (50 mg, 291 μmol) were coupled according to the GP4. The product was obtained as a grey solid (82 mg, 66%). $^1H$ NMR (400 MHz, DMSO-$d_6$) δ 10.41 (s, 1H), 10.25 (s, 1H), 8.40 (s, 1H), 8.16 (t, J=1.7 Hz, 1H), 7.98 (d, J=7.9 Hz, 1H), 7.81 (d, J=8.9 Hz, 1H), 7.69 (s, 1H), 7.60-7.47 (m, 3H), 3.55-3.44 (m, 1H), 1.99 (s, 3H), 1.20 (t, J=7.1 Hz, 3H); $^{13}C$ NMR (100 MHz, DMSO-$d_6$) δ 164.32, 162.31, 151.60, 137.51, 135.93, 134.82, 133.44, 131.19, 130.76, 127.38, 122.22, 121.47, 107.18, 89.02, 36.73, 14.44, 13.44; MS ($ESI^+$) m/z 426 ($^{79}Br$ $M^++H^+$, 100), 428 ($^{81}Br$ $M^++H^+$, 94); HRMS calculated for $C_{20}H_{21}{}^{79}BrN_5O$ ($M^++H^+$) 426.0929 found 426.0922 (−1.6 PPM); FTIR (nujol, $cm^{-1}$) $\nu_{max}$ 1666, 1205, 829, mp: >230° C.

3-bromo-N-(4-((4-(diethylamino)-6-methylpyrimidin-2-yl)amino)phenyl)benzamide (Br DE)

N-(4-Aminophenyl)-3-bromobenzamide (BA2) (644 mg, 2.21 mmol) was coupled with 2-chloro-N,N-diethyl-6-methylpyrimidin-4-amine (PY6) (442 mg, 2.21 mmol) according to the GP4. The product was obtained as a black solid (965 mg, 97%); $^1H$ NMR (396 MHz, DMSO-$d_6$) δ 9.97 (s, 1H), 8.10 (s, 1H), 7.92 (d, J=7.8 Hz, 1H), 7.75 (d, J=8.0 Hz, 1H), 7.47 (t, J=7.9 Hz, 1H), 7.37 (d, J=8.7 Hz, 2H), 6.59-6.51 (m, 3H), 5.01 (s, 2H), 3.60-3.47 (m, J=14.2, 7.3 Hz, 4H), 2.26 (s, 3H), 1.10 (t, J=7.0 Hz, 6H); $^{13}C$ NMR (100 MHz, DMSO-$d_6$) δ 170.0, 163.5, 160.8, 160.4, 145.9, 138.0, 134.3, 131.0, 130.5, 128.3, 127.1, 122.7, 122.1, 114.1, 107.6, 100.0, 41.8, 24.2, 13.3; FTIR (nujol, $cm^{-1}$) $\nu_{max}$ 3304, 1645, 1118, 889, 590; MS ($ESI^+$) m/z 454 ($^{79}Br$ $M^++H^+$, 100), 456 ($^{81}Br$ $M^++H^+$, 88); HRMS calculated for $C_{22}H_{25}{}^{81}BrN_5O$ ($M^++H^+$) 456.1222; found 456.1245 (5.0 PPM); mp: 97-101° C.

3-bromo-N-(4-((4-methyl-6-(methylamino)pyrimidin-2-yl)amino)phenyl)benzamide (Br Me)

N-(4-Aminophenyl)-3-bromobenzamide (BA2) (388 mg, 1.33 mmol) and 2-chloro-N-methyl-6-methylpyrimidin-4-amine (210 mg, 1.33 mmol) were coupled according to the GP4. The product was obtained as a light blue solid (472 mg, 86%). $^1H$ NMR (396 MHz, DMSO-$d_6$) δ 10.42 (s, 1H), 10.28 (s, 1H), 8.96 (s, 1H), 8.15 (d, J=1.5 Hz, 1H), 7.97 (d, J=7.8 Hz, 1H), 7.80 (d, J=7.9 Hz, 3H), 7.59 (d, J=8.9 Hz, 2H). 7.50 (t, J=7.9 Hz, 1H), 6.04 (s, 1H), 2.26 (s, J=25.6 Hz, 3H). $^{13}C$ NMR (100 MHz, DMSO-$d_6$) δ 164.3, 163.6, 152.9, 137.5, 135.7, 134.8, 133.4, 131.1, 130.7, 127.3, 122.2, 121.7, 121.5, 97.2, 28.1, 18.8; MS ($ESI^+$) m/z 412 ($^{79}Br$ $M^++H^+$, 100), 414 ($^{81}Br$ $M^++H^+$, 74); HRMS calculated for $C_{19}H_{19}{}^{79}BrN_5O$ ($M^++H^+$) 412.0773; found 412.0786 (3.2 PPM); FTIR (nujol, $cm^{-1}$) $\nu_{max}$ 3442, 1658, 1118, 835; mp: 301-303° C.

3-bromo-N-(4-((2-(ethylamino)-6-methylpyrimidin-4-yl)amino)phenyl)benzamide (Br U Et iso)

N-(4-Aminophenyl)-3-bromobenzamide (BA2) (300 mg, 1.03 mmol) and 4-chloro-N-ethyl-6-methylpyrimidin-2-amine (PY5) (177 mg, 1.03 mmol) were coupled according to the GP4. The product was obtained as a colourless solid (352 mg, 80%). $^1H$ NMR (400 MHz, DMSO-$d_6$) δ 10.81 (s, 1H), 10.45 (s, 1H), 8.15 (s, 1H), 7.97 (d, J=7.9 Hz, 1H), 7.93-7.59 (m, 6H), 7.50 (t, J=7.9 Hz, 1H), 6.17 (s, 1H), 2.28 (s, 3H), 1.17 (t, J=7.1 Hz, 3H). $^{13}C$ NMR (100 MHz, DMSO-$d_6$) δ 164.4, 154.7, 137.5, 134.8, 131.2, 130.8, 127.4, 122.2, 122.0, 121.9, 121.3, 36.36, 18.98, 14.73; MS ($ESI^+$) m/z 426 ($^{79}Br$ $M^++H^+$, 100), 428 ($^{81}Br$ $M^++H^+$, 88); HRMS calculated for $C_{20}H_{11}{}^{79}BrN_5O$ ($M^++H^+$) 426.0817; found 426.0838 (4.9 PPM); FTIR (nujol, $cm^{-1}$) $\nu_{max}$ 3240, 1666, 842, 524; mp: 260-264° C.

3-bromo-N-(4-((4-(ethylamino)-6-methylpyrimidin-2-yl)amino)phenyl)benzamide (Cpd 6)

N-(4-Aminophenyl)-3-bromobenzamide (BA2) (300 mg, 1.03 mmol) and 2-chloro-N-ethyl-6-methylpyrimidin-4-amine (176 mg, 1.03 mmol) were coupled according to the GP4. The product was obtained as a light grey solid (439 mg, 80%). $^1H$ NMR (400 MHz, DMSO-$d_6$) δ 10.37 (s, 1H), 10.28 (s, 1H), 8.87 (s, 1H), 8.14 (d, J=1.5 Hz, 1H), 7.95 (d, J=7.8 Hz, 1H), 7.83-7.70 (m, J=15.5, 9.0 Hz, 3H), 7.55 (d, J=8.9 Hz, 2H), 7.46 (t, J=7.9 Hz, 1H), 5.98 (s, 1H), 3.46-3.30 (m, 2H), 2.23 (s, 3H), 1.15 (t, J=7.2 Hz, 3H); $^{13}C$ NMR (100 MHz, DMSO-$d_6$) δ 164.3, 162.8, 152.8, 151.7, 137.5, 135.8, 134.8, 133.4, 131.1, 130.7, 127.3, 122.2, 121.6, 121.4, 97.5, 36.2, 18.8, 14.3; MS ($ESI^+$) m/z 426 ($^{79}Br$ $M^+$+$H^+$, 100), 428 ($^{81}$Br $M^+$+$H^+$, 85); HRMS calculated for $C_{20}H_{21}{}^{81}BrN_5O$ ($M^+$+$H^+$) 412.0909; found 412.0898 (−2.6 PPM); FTIR (nujol, $cm^{-1}$) $\nu_{max}$ 1658, 1116, 869, 599; mp: 227° C.

Cpd 6 Commercially Obtained Reference Spectrum $^1$H NMR (400 MHz, DMSO-$d_6$) δ 10.36 (s, 1H), 9.85 (s, 1H), 8.34 (s, 1H), 8.16 (s, 1H), 7.98 (d, J=7.8 Hz, 1H), 7.79 (d, J=8.4 Hz, 1H), 7.74 (d, J=8.8 Hz, 2H), 7.65 (d, J=8.8 Hz, 2H), 7.50 (t, J=7.9 Hz, 1H), 5.96 (s, 1H), 2.22 (s, 3H), 1.17 (t, J=7.2 Hz, 3H).

ethyl (2-((4-(3-bromobenzamido)phenyl)amino)-6-methylpyrimidin-4-yl)glycinate (Br Gly)

N-(4-Aminophenyl)-3-bromobenzamide (BA2) (507 mg, 1.74 mmol) and ethyl (2-chloro-6-methylpyrimidin-4-yl) glycinate (400 mg, 1.74 mmol) were coupled according to the GP4. The product was obtained as a light grey solid (585 mg, 69%). $^1$H NMR (400 MHz, DMSO-$d_6$) δ 10.42 (s, 1H), 10.02 (s, 1H), 9.25 (s, 1H), 8.15 (s, 1H), 7.97 (d, J=7.8 Hz, 1H), 7.86-7.76 (m, J=7.7, 4.3, 2.8 Hz, 3H), 7.52 (t, J=7.9 Hz, 1H), 7.48 (d, J=8.9 Hz, 2H), 6.20 (s, 1H), 4.18 (s, J=5.9 Hz, 2H), 4.11 (d, J=7.1 Hz, 2H), 2.32 (s, 3H), 1.19 (t, J=7.1 Hz, 2H); $^{13}$C NMR (100 MHz, DMSO-$d_6$) δ 169.5, 164.3, 163.7, 137.5, 134.8, 131.2, 130.7, 127.3, 122.2, 121.9, 121.1, 97.3, 61.3, 43.0, 39.8, 39.6, 39.4, 19.1, 14.5; MS ($ESI^+$) m/z 484 ($^{79}$Br $M^+$+$H^+$, 100), 486 ($^{81}$Br $M^+H^+$, 94); HRMS calculated for $C_{22}H_{23}{}^{81}BrN_5O_3$ ($M^+$+$H^+$) 486.0964; found 486.0970 (1.2 PPM); FTIR (nujol, $cm^{-1}$) $\nu_{max}$ 3331, 1726, 1668, 642; mp: >230° C.

3-bromo-N-(4-((4(4-((2-hydroxyethyl)amino)-6-methylpyrimidin-2-yl)amino)phenyl)benzamide (Br Et OH)

N-(4-Aminophenyl)-3-bromobenzamide (BA2) (310 mg, 1.07 mmol) and 2-((2-chloro-6-methylpyrimidin-4-yl) amino)ethan-1-ol (PY12) (200 mg, 1.07 mmol) were coupled according to the GP4. The product was obtained as a light blue solid (86 mg, 18%). $^1$H NMR (400 MHz, DMSO-$d_6$) δ 10.43 (s, 1H), 10.25 (s, 1H), 9.00 (s, 1H), 8.16 (s, 1H), 7.98 (d, J=8.0 Hz, 1H), 7.80 (d, J=8.7 Hz, 3H), 7.57 (d, J=8.3 Hz, 2H), 7.50 (t, J=7.9 Hz, 1H), 6.07 (s, 1H), 4.93 (s, 1H), 3.58 (m, 2H), 3.48 (m, 2H), 2.26 (s, 3H); $^{13}$C NMR (100 MHz, DMSO-$d_6$) δ 164.3, 163.4, 153.1, 152.3, 137.5, 135.6, 134.8, 133.6, 133.6, 131.2, 130.8, 127.4, 122.6, 122.2, 121.5, 97.4, 59.5, 44.2, 19.1; MS ($ESI^+$) m/z ($^{79}$Br $M^+$+$H^+$, 100), ($^{81}$Br $M^+$+$H^+$, 95); HRMS calculated for $C_{20}H_{21}BrN_5O_2$ ($M^+$+$H^+$) 442.0879; found 442.0864 (−3.4 PPM); mp: 237-241° C.

3-bromo-N-(4-((4-(isopropylamino)-6-methylpyrimidin-2-yl)amino)phenyl)benzamide (Br iso)

N-(4-Aminophenyl)-3-bromobenzamide (BA2) (300 mg, 1.03 mmol) and 2-chloro-N-isopropyl-6-methylpyrimidin-4-amine (PY10) (191 mg, 1.03 mmol) were coupled according to the GP4. The product was obtained as black crystals (240 mg, 53%). $^1$H NMR (400 MHz, DMSO-$d_6$) δ 10.40 (s, 1H), 10.04 (s, 1H), 8.75 (s, 1H), 8.15 (s, 1H), 7.97 (d, J=7.7 Hz, 1H), 7.86-7.61 (m, J=7.1, 4.9 Hz, 4H), 7.68-7.35 (m, J=14.4, 8.2 Hz, 4H), 5.98 (s, 1H), 4.14 (s, 1H), 2.26 (s, 3H), 1.20 (d, J=6.5 Hz, 6H); MS ($ESI^+$) m/z 440 ($^{79}$Br $M^+$+$H^+$, 100), 442 ($^{81}$Br $M^+$+$H^+$, 95); HRMS calculated for $C_{21}H_{23}{}^{79}BrN_5O$ ($M^+$+$H^+$) 440.1086; found 440.1103 (3.9 PPM); FTIR (nujol, $cm^{-1}$) $\nu_{max}$ 2320, 1666, 1573, 1155, 837, 480; mp: 183-185° C.

N-(4-((4-(ethylamino)-6-methylpyrimidin-2-yl)amino)phenyl)benzamide (H U Et)

N-(4-Aminophenyl)benzamide (BA4) (300 mg, 1.41 mmol) and 2-chloro-N-ethyl-6-ethyl-pyrimidin-4-amine (243 mg, 1.41 mmol) were coupled according to the GP4. The product was obtained as grey solid (204 mg, 42%). $^1$H NMR (400 MHz, DMSO-$d_6$) δ 10.38 (s, 1H), 10.15 (s, 1H), 8.91 (s, 1H), 8.11 (s, 1H), 7.93 (d, J=7.7 Hz, 1H), 7.76 (d, J=8.0 Hz, 3H), 7.53 (d, J=8.0 Hz, 2H), 7.47 (t, J=7.9 Hz, 1H), 5.97 (s, 1H), 2.22 (s, 3H), 1.13 (t, J=7.3 Hz, 3H); $^{13}$C NMR (100 MHz, DMSO-$d_6$) δ 165.9, 162.2, 152.5, 140.7, 135.7, 135.4, 133.9, 132.1, 128.9, 128.2, 121.5, 121.4, 106.8, 71.78, 40.7, 40.5, 40.3, 40.1, 39.8, 39.6, 39.4, 36.6, 34.2, 14.5, 13.5; MS ($ESI^+$) m/z 348 ($M^+$+$H^+$); HRMS calculated for $C_{20}H_{22}N_5O$ ($M^+$+$H^+$) 348.1824; found 348.1841 (4.9 PPM); FTIR (nujol, $cm^{-1}$) $\nu_{max}$ 1658, 1579, 1255, 835, 476; mp: 225-226° C.

N-(4-((4-(ethylamino)-5-methylpyrimidin-2-yl)amino)phenyl)benzamide (H T Et)

N-(4-Aminophenyl)benzamide (BA4) (74 mg, 350 μmol) and 2-chloro-N-ethyl-5-methylpyrimidin-4-amine (60 mg, 350 μmol) were coupled according to the GP4. The product was obtained as a colourless solid (78 mg, 64%). $^1$H NMR (400 MHz, DMSO-$d_6$) δ 10.31 (s, 1H), 10.23 (s, 1H), 8.33 (s, 1H), 7.97 (d, J=6.9 Hz, 2H), 7.81 (d, J=5.6 Hz, 2H), 7.68 (s, 1H), 7.63-7.56 (m, 1H), 7.54 (d, J=7.7 Hz, 4H), 3.58-3.36 (q, J=7.0 Hz, 2H), 1.98 (s, 3H), 1.20 (t, J=7.0 Hz, 3H); $^{13}$C NMR (100 MHz, DMSO-$d_6$) δ 165.9, 162.9, 152.8, 151.9, 136.2, 135.4, 133.2, 132.1, 128.9, 128.2, 121.8, 121.4, 97.3, 36.3, 18.8, 14.4; MS ($ESI^+$) m/z 348 ($M^+$+$H^+$); HRMS calculated for $C_{20}H_{22}N_5O$ ($M^+$+$H^+$) 348.1824; found 348.1822 (−0.6 PPM); mp>230° C.

N-(4-((4-(ethylamino)-6-methylpyrimidin-2-yl)amino)phenyl)-3-fluorobenzamide (F U Et)

N-(4-Aminophenyl)-3-fluorobenzamide (BA6) (300 mg, 1.30 mmol) and 2-chloro-N-ethyl-6-methylpyrimidin-4-amine (223 mg, 1.30 mmol) were coupled according to the GP4. The product was obtained as a colourless solid (272 mg, 68%). $^1$H NMR (400 MHz, DMSO-$d_6$) δ 10.41 (s, 1H), 10.28 (s, 1H), 9.02 (s, 1H) 7.88-7.75 (m, 4H), 7.68-7.49 (m, 3H), 7.45 (t, J=7.3 Hz, 1H), 6.03 (s, 1H), 3.50-3.39 (m, 2H), 2.27 (s, 3H), 1.18 (t, J=7.2 Hz, 3H); $^{13}$C NMR (100 MHz, DMSO-$d_6$) δ 164.5 (d, J=2.0 Hz), 162.5 (d, J=244.3 Hz), 152.8, 151.9, 137.7 (d, J=6.7 Hz), 133.4, 131.1 (d, J=8.0 Hz), 124.4, 121.7, 121.5, 119.0 (d, J=20.7 Hz), 115.0 (d, J=22.8 Hz), 97.2, 36.2, 18.8, 14.3; MS ($ESI^+$) m/z 366 ($M^+$+$H^+$); HRMS calculated for $C_{20}H_{21}FN_5O$ ($M^+$+$H^+$) 366.1730; found 366.1734 (3.6 PPM); FTIR (nujol, $cm^{-1}$) $\nu_{max}$ 1660, 1631, 1236, 1199, 839; mp: 259-263° C.

N-(4-((4-(ethylamino)-5-methylpyrimidin-2-yl)amino)phenyl)-3-fluorobenzamide (F T Et)

N-(4-Aminophenyl)-3-fluorobenzamide (BA6) (70 mg, 304 μmol) and 2-chloro-N-ethyl-5-methylpyrimidin-4-amine (52 mg, 304 μmol) were coupled according to the GP4. The product was obtained as a colourless solid (272 mg, 68%).

The product was obtained as a colourless solid (45 mg, 41%). $^1$H NMR (400 MHz, DMSO-$d_6$) δ 10.27 (s, 1H), 9.94 (s, 1H), 7.96-7.47 (m, 5H), 7.37 (d, J=8.7 Hz, 2H), 6.57 (d, J=8.8 Hz, 2H), 6.22 (s, 1H), 5.40 (s. 1H), 2.16 (s, 3H), 1.09 (t, J=7.2 Hz, 3H); $^{13}$C NMR (100 MHz, DMSO-$d_6$) δ

164.47, 163.0, 162.5 (d, J=244.4 Hz), 153.0, 137.7, 135.7, 133.6, 131.1 (d, J=8.3 Hz 124.4, 122.2, 121.6, 121.5, 118.9 (d, J=20.7 Hz), 115.0 (d, J=22.9 Hz), 97.2, 36.3, 19.0, 14.4; MS ($ESI^+$) m/z 366 ($M^+$+$H^+$); HRMS calculated for $C_{20}H_{21}FN_5O$ ($M^+$+$H^+$) 366.1730; found 366.1754 (6.6 PPM); FTIR (nujol, $cm^{-1}$) $\nu_{max}$ 13543, 1660, 1595, 1265; mp: >230° C.

N-(4-((4-(ethylamino)-6-methylpyrimidin-2-yl)amino)phenyl)-3-hydroxybenzamide (3OH U Et)

N-(4-Aminophenyl)-3-hydroxybenzamide (BA14) (250 mg, 1.10 mmol) and 2-chloro-N-methyl-6-ethylpyrimidin-4-amine (187 mg, 1.10 mmol) were coupled according to the GP4. The product was obtained as a colourless solid (272 mg, 68%). $^1$H NMR (396 MHz, DMSO-$d_6$) δ 10.22 (s, 2H), 9.79 (s, 1H), 8.99 (s, 1H), 7.80 (d, J=8.8 Hz, 2H), 7.53 (d, J=8.8 Hz, 2H), 7.38 (d, J=7.8 Hz, 1H), 7.35-7.26 (m, J=10.2, 5.5 Hz, 2H), 6.98 (d, J=6.2 Hz, 1H), 6.01 (s, 1H), 2.26 (s, 3H), 1.17 (t, J=7.3 Hz, 3H); $^{13}$C NMR (100 MHz, DMSO-$d_6$) δ 165.9, 162.8, 157.9, 152.8, 151.9, 136.8, 136.2, 133.0, 129.9, 121.7, 121.3, 119.0, 118.6, 115.0, 97.2, 45.9, 36.2, 18.8, 14.3, 8.9; MS ($ESI^+$) m/z 364 ($M^+$+$H^+$); HRMS calculated for $C_{20}H_{23}N_5O_2$ ($M^+$+$H^+$) 364.1174; found 364.1768 (−1.6 PPM); FTIR (nujol, $cm^{-1}$) $\nu_{max}$ 1666, 1531, 1323, 835, 478; mp: 283-285° C.

N-(4-((4-(ethylamino)-6-methylpyrimidin-2-yl)amino)phenyl)-4-methylbenzamide (4 Me U Et)

N-(4-Aminophenyl)-4-methylbenzamide (BA8) (250 mg, 1.10 mmol) and 2-chloro-N-ethyl-6-methylpyrimidin-4-amine (187 mg, 1.10 mmol) were coupled according to the GP4. The product was obtained as a colourless solid (272 mg, 68%). $^1$H NMR (396 MHz, DMSO-$d_6$) δ 10.27 (s, J=14.1 Hz, 1H), 10.23 (s, 1H), 9.02 (s, 1H), 7.89 (d, J=7.8 Hz, 2H), 7.81 (d, J=8.6 Hz, 2H), 7.54 (d, J=8.6 Hz, 2H), 7.33 (d, J=7.9 Hz, 2H), 6.02 (s, 1H), 3.48-3.38 (m, 2H), 2.39 (s, 3H), 2.26 (s, 3H), 1.17 (t, J=7.1 Hz, 3H); $^{13}$C NMR (100 MHz, DMSO-$d_6$) δ 165.7, 162.8, 152.8, 142.0, 136.2, 133.0, 132.4, 129.4, 128.2, 121.7, 121.3, 97.2, 40.69, 36.24, 21.54, 18.84, 14.38; MS ($ESI^+$) m/z 362 ($M^+$+$H^+$); HRMS calculated for $C_{21}H_{24}N_5O$ ($M^+$+$H^+$); 362.1981; found 362.1971 (−2.8 PPM); FTIR (nujol, $cm^{-1}$) $\nu_{max}$ 3446, 1662, 1573, 840, 744; mp: 297-300° C.

N-(4-((4-(ethylamino)-6-methylpyrimidin-2-yl)amino)phenyl)-4-methoxybenzamide (4OMe U Et)

N-(4-Aminophenyl)-4-methoxybenzamide (BA10) (250 mg, 1.10 mmol) and 2-chloro-N-methyl-6-ethylpyrimidin-4-amine (187 mg, 1.10 mmol) were coupled according to the GP4. The product was obtained as a colourless solid (472 mg, 86%). $^1$H NMR (400 MHz, DMSO-$d_6$) δ 10.27 (s, 1H), 10.17 (s, 1H), 9.01 (s, 1H), 8.08-7.91 (m, 2H), 7.80 (d, J=8.4 Hz, 2H), 7.54 (d, J=8.3 Hz, 2H), 7.06 (d, J=7.7 Hz, 2H), 6.02 (s, 1H), 3.84 (s, 3H), 2.26 (s, J=12.9 Hz, 3H), 1.17 (t, J=7.6 Hz, 3H); $^{13}$C NMR (100 MHz, DMSO-$d_6$) δ 165.27, 162.89, 162.42, 152.91, 151.96, 136.35, 132.98, 130.11, 127.38, 121.71, 121.36, 114.13, 100.41, 97.21, 45.91, 36.23, 23.77, 14.39, 8.98; MS ($ESI^+$) m/z 378 ($M^+$+$H^+$); HRMS calculated for $C_{21}H_{24}N_5O_2$ ($M^+$+$H^+$) 378.1930; found 378.1941 (2.9 PPM); FTIR (nujol, $cm^{-1}$) $\nu_{max}$ 3429, 1633, 1024, 835; mp: 285-288° C.

3-bromo-N-(4-((4-(ethylamino)pyrimidin-2-yl)amino)phenyl)benzamide (Br desMe)

N-(4-Aminophenyl)-3-bromobenzamide (BA2) (300 mg, 1.03 mmol) and 2-chloranylpyrimidin-4-amine (162 mg, 1.03 mmol) were coupled according to the GP4. The product was obtained as a light brown solid (306 mg, 72%). $^1$H NMR (400 MHz, DMSO-$d_6$) δ 12.07 (s, 1H), 10.74 (s, 1H), 10.48 (s, 1H), 9.25 (s, 1H), 8.17 (s, 1H), 7.99 (d, J=7.7 Hz, 1H), 7.90-7.69 (m, J=13.2, 8.9 Hz, 4H), 7.68-7.39 (m, J=15.7, 11.6 Hz, 3H), 6.23 (d, J=7.2 Hz, 1H), 3.46-3.39 (m, J=6.9 Hz, 2H), 1.18 (t, J=7.2 Hz, 3H); $^{13}$C NMR (100 MHz, DMSO-$d_6$) δ 164.35, 152.43, 141.68, 137.50, 134.83, 131.20, 130.77, 127.40, 122.22, 121.49, 99.06, 74.55, 40.68, 36.22, 14.25; MS ($ESI^+$) m/z 412 ($^{79}$Br $M^+$+$H^+$, 100), 414 ($^{81}$Br $M^+$+$H^+$, 95); HRMS calculated for $C_{19}H_{20}{}^{79}BrN_5O$ ($M^+$+$H^+$) 412.0773; found 412.0775 (0.5 PPM); FTIR (nujol, $cm^{-1}$) $\nu_{max}$ 3417, 1670, 831; mp: 229-231° C.

Minimum Inhibitory Concentration Determination

The broth micro dilution method was used to determine the minimum inhibitory concentration (MIC) of the test compounds. Two fold serial dilutions of the compounds were made with 7H9 broth. Each concentration was assayed in triplicates. The diluted test inoculum of *M. smegmatis* mc$^2$ 155 (200 μl) was added to all the wells in the microplate and was incubated at 37° C. for 24 hours. The final OD of the cultures in the plate was measured by Tecan Infinite 200 PRO plate reader.

MIC determination of drugs against *M. tuberculosis* H37Rv and *Mycobacterium bovis* BCG was done in test tubes with two-fold serial dilution from 200-0.1 μM. The diluted test inoculum (1 ml) was added to the test tubes and incubated on the orbital shaker at 37° C. for 5-8 days. The final OD of the cultures in the plate was measured by a Tecan Infinite 200 PRO plate reader. The $MIC_{50}$ was defined as the drug concentration that inhibited 50% of the bacterial growth when compared to the growth in the drug-free medium.

The present invention provides compounds that inhibit the $F_1F_O$-ATP synthase and the use of said compounds with or without bedaquiline (BDQ) or Q203 in a multi-drug regimen for the treatment of MDR-TB and XDR-TB.

Figure 2A:
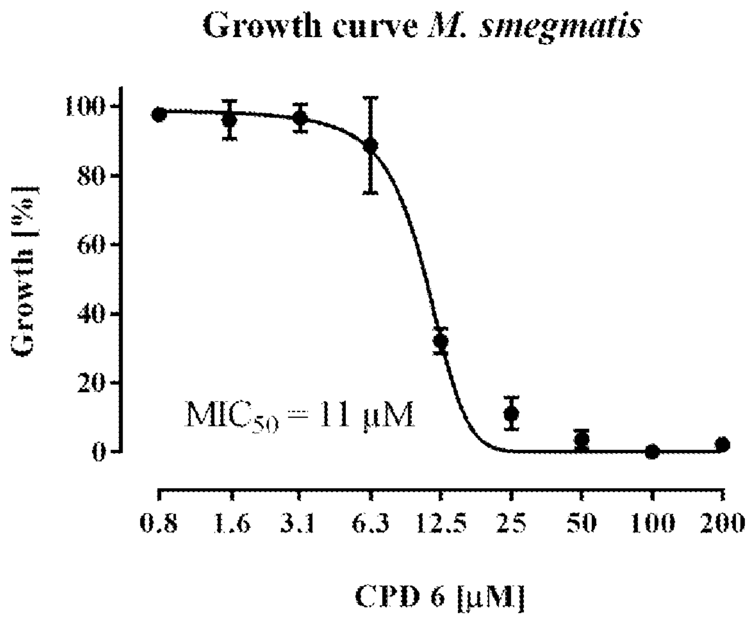
FIG. 2A illustrates that cpd 6 inhibited *M. smegmatis* growth with an $MIC_{50}$ value of 11 μM.
Figure 2B:
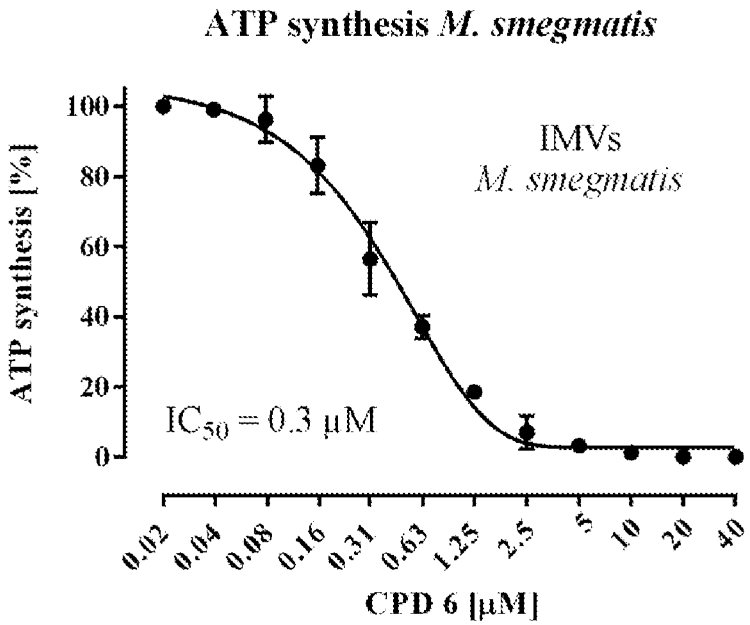
FIG. 2B illustrates that cpd 6 blocked ATP synthesis with an $IC_{50}$ value of 0.3 μM (or 300 nM)
Figure 2C:
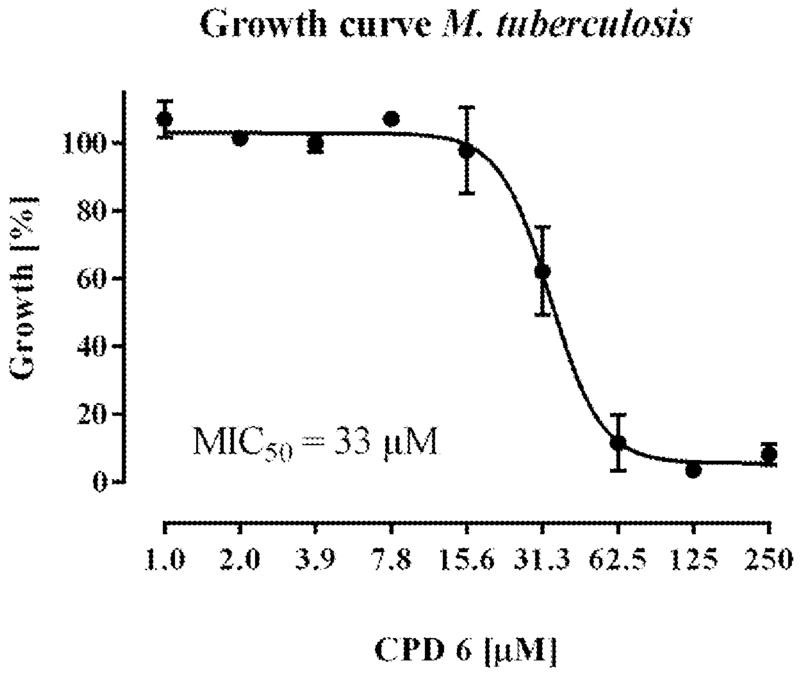
FIG. 2C illustrates that cpd 6 inhibited *M. tuberculosis* H37Rv growth with an $MIC_{50}$ value of 33 μM.
Figure 2D:
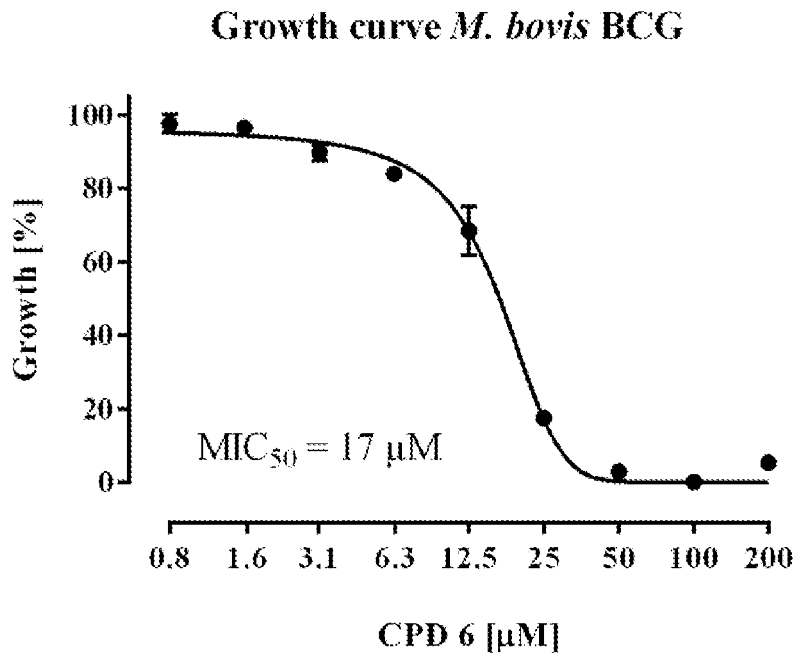
FIG. 2D illustrates that cpd 6 inhibited *M. bovis* BCG growth with an $MIC_{50}$ value of 17 μM.

Based on a homology model of the yeast F-ATP synthase and structural information of the novel mycobacterial subunit γ extension from our lab (Priya, R., et al. Solution structure of subunit gamma (gamma(1-204)) of the *M. tuberculosis* F-ATP synthase and the unique loop of gamma (165-178), representing a novel TB drug target. *J. Bioenerg. Biomembr.* 45, 121-129 (2013)), a homology model was generated. With this model, we virtually docked 1.5 million compounds. The 81 best scoring compounds were tested for the growth inhibition and compound 6 (cpd 6) inhibited *M. smegmatis* growth with an $MIC_{50}$ of 11 μM (Table 1, FIG. 2A), cpd 6 blocked ATP synthesis with an $IC_{50}$ value of about 300 nM (FIG. 2B) and inhibited ATP hydrolysis activity in a manner comparable to known ATPase inhibitors growth of *M. bovis* BCG with a $MIC_{50}$ of 17 μM (FIG. 2D), and *M. tuberculosis* H37Rv with a $MIC_{50}$ of 33 μM (FIG. 2C). These data confirmed that cpd 6 affects the activity of the central biological energy converter F-ATP synthase of mycobacteria. Subsequently a series of analogs of cpd 6 were synthesized, guided by the model of the docked compound to the F-ATP synthase.

The analogs of cpd 6 have the general structure as follows:

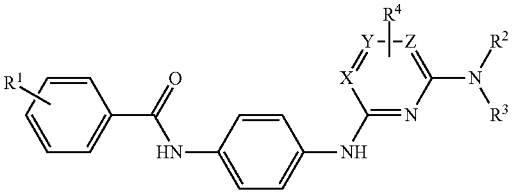

wherein $R^1$=3-Br, 3-F, 3-OH, 4-Me, 4-OMe, H;

$R^2$=$CH_2CH_2OH$, $-CH_2COOEt$, Me, Et, i-Pr; and $R^3$=H and $R^4$=Me.

Alternatively, the analogs could be a uracil isomer (different N position) of cpd 6 with the general structure as follows:

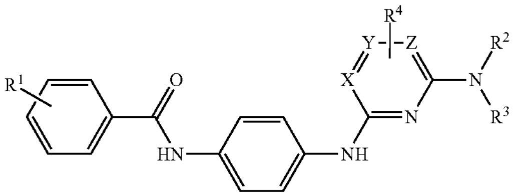

wherein $R^1$=H, halogen, $C_1$-$C_4$ alkyl, $C_1$-$C_4$ alkoxy, OH;

$R^2$=H, $C_1$-$C_4$ alkyl, $C_1$-$C_4$alkyl alcohol, $C_1$-$C_4$alkoxy, $-CH_2COOEt$;

$R^3$=H, Et;

$R^4$=H, halogen, $C_1$-$C_4$ alkyl, $C_1$-$C_4$ alkoxy;

X, Y and Z are independently C or N.

TABLE 1

Newly synthesized molecules and their effect on ATP synthesis ($IC_{50}$) and bacterial growth ($MIC_{50}$)

| | Name | Structure | commer. available | synthesis known | $IC_{50}$ [μM] | $MIC_{50}$ [μM] |
|---|---|---|---|---|---|---|
| 1 | Cpd 6 | 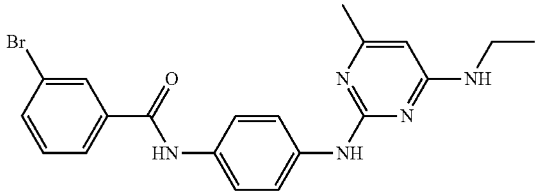 [SMILES: CCNc1cc(C)nc(Nc2ccc(NC(=O)c3cccc(Br)c3)cc2)n1] | yes | no | 0.30 ± 0.02 | 10.77 ± 0.43 |
| 2 | H U Et | 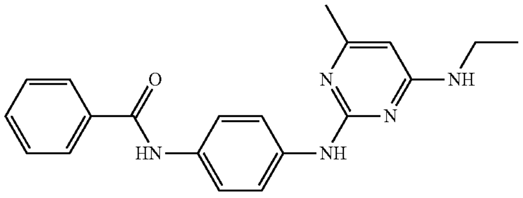 [SMILES: CCNc1cc(C)nc(Nc2ccc(NC(=O)c3ccccc3)cc2)n1] | yes | no | 1.65 ± 0.16 | 26.94 ± 1.39 |
| 3 | H T Et | 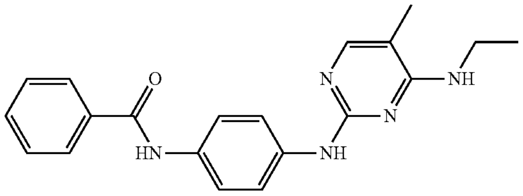 [SMILES: CCNc1nc(Nc2ccc(NC(=O)c3ccccc3)cc2)ncc1C] | no | no | 0.90 ± 0.06 | 39.0 ± 1.91 |
| 4 | F U Et | 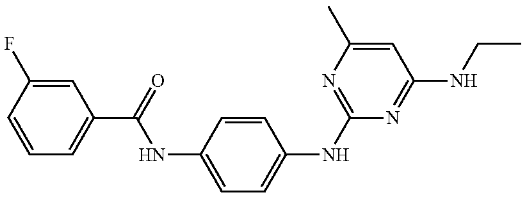 [SMILES: CCNc1cc(C)nc(Nc2ccc(NC(=O)c3cccc(F)c3)cc2)n1] | yes | no | 0.26 ± 0.05 | 18.72 ± 1.25 |

TABLE 1-continued
Newly synthesized molecules and their effect on ATP synthesis ($IC_{50}$) and bacterial growth ($MIC_{50}$)
| | Name | Structure | commer. available | synthesis known | $IC_{50}$ [μM] | $MIC_{50}$ [μM] |
|---|---|---|---|---|---|---|
| 5 | F T Et | 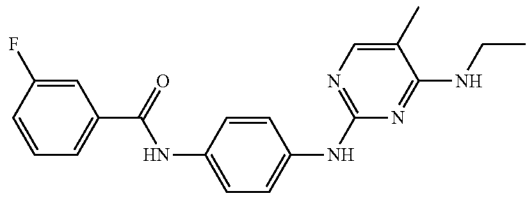 [SMILES: CCNc1nc(Nc2ccc(NC(=O)c3cccc(F)c3)cc2)ncc1C] | no | no | 0.92 ± 0.04 | 43.51 ± 3.57 |
| 6 | Br T Et | 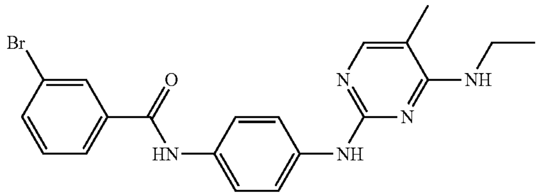 [SMILES: CCNc1nc(Nc2ccc(NC(=O)c3cccc(Br)c3)cc2)ncc1C] | no | no | 0.62 ± 0.08 | 12.32 ± 0.73 |
| 7 | Br U Et iso (Cpd 6 iso) | 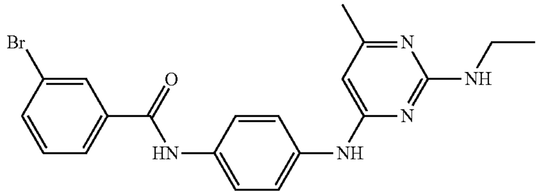 [SMILES: CCNc1nc(C)cc(Nc2ccc(NC(=O)c3cccc(Br)c3)cc2)n1] | no | no | 0.38 ± 0.03 | 20.82 ± 1.90 |
| 8 | Br Gly | 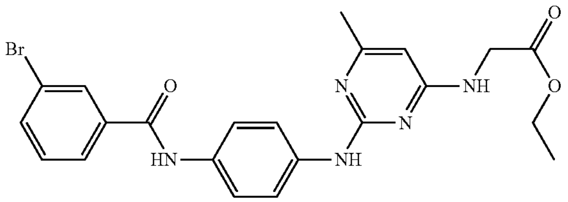 [SMILES: CCOC(=O)CNc1cc(C)nc(Nc2ccc(NC(=O)c3cccc(Br)c3)cc2)n1] | no | no | 2.01 ± 0.16 | 15.54 ± 1.52 |
| 9 | Br EtOH | 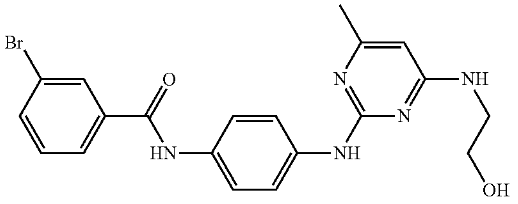 [SMILES: Cc1cc(NCCO)nc(Nc2ccc(NC(=O)c3cccc(Br)c3)cc2)n1] | no | no | 0.42 ± 0.03 | 19.02 ± 1.50 |
| 10 | Br DE | 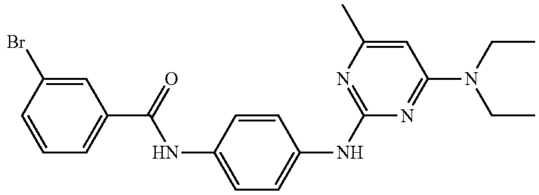 [SMILES: CCN(CC)c1cc(C)nc(Nc2ccc(NC(=O)c3cccc(Br)c3)cc2)n1] | yes | no | 10.8 ± 2.8 | 75.79 ± 13.15 |
| 11 | Br Me | 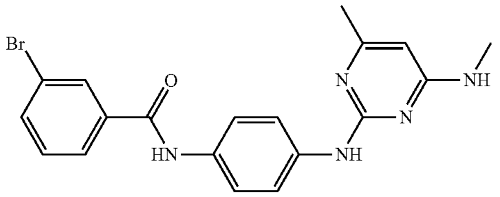 [SMILES: CNc1cc(C)nc(Nc2ccc(NC(=O)c3cccc(Br)c3)cc2)n1] | no | no | 0.39 ± 0.06 | 12.4 ± 0.56 |

TABLE 1-continued

Newly synthesized molecules and their effect on ATP synthesis ($IC_{50}$) and bacterial growth ($MIC_{50}$)

| | Name | Structure | commer. available | synthesis known | $IC_{50}$ [μM] | $MIC_{50}$ [μM] |
|---|---|---|---|---|---|---|
| 12 | Br iso | 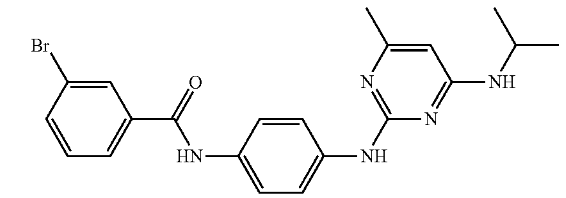 [SMILES: Cc1cc(NC(C)C)nc(Nc2ccc(NC(=O)c3cccc(Br)c3)cc2)n1] | no | no | 2.69 ± 0.21 | 50.1 ± 4.5 |
| 13 | Br desMe | 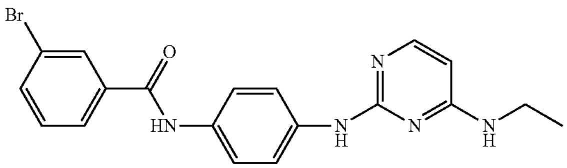 [SMILES: CCNc1ccnc(Nc2ccc(NC(=O)c3cccc(Br)c3)cc2)n1] | no | no | 1.03 ± 0.25 | 16.82 ± 2.6 |
| 14 | 3OH U Et | 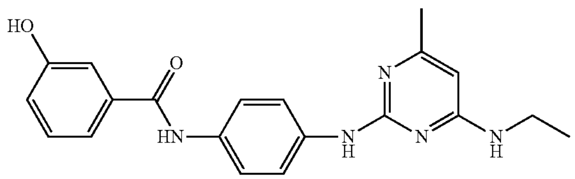 | no | no | 1.16 ± 0.09 | 79.57 ± 9.13 |
| 15 | 4Me U Et | 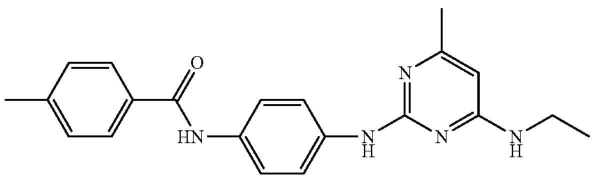 [SMILES: CCNc1cc(C)nc(Nc2ccc(NC(=O)c3ccc(C)cc3)cc2)n1] | yes | no | 0.39 ± 0.02 | 31.76 ± 7.8 |
| 16 | 4OMe U Et | 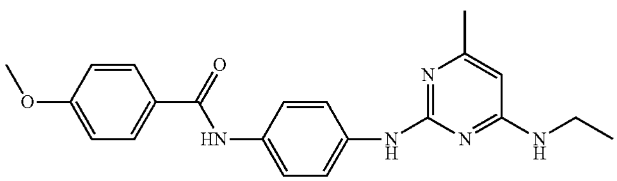 [SMILES: CCNc1cc(C)nc(Nc2ccc(NC(=O)c3ccc(OC)cc3)cc2)n1] | yes | no | 0.69 ± 0.06 | 17.28 ± 2.26 |

Figure 3A:
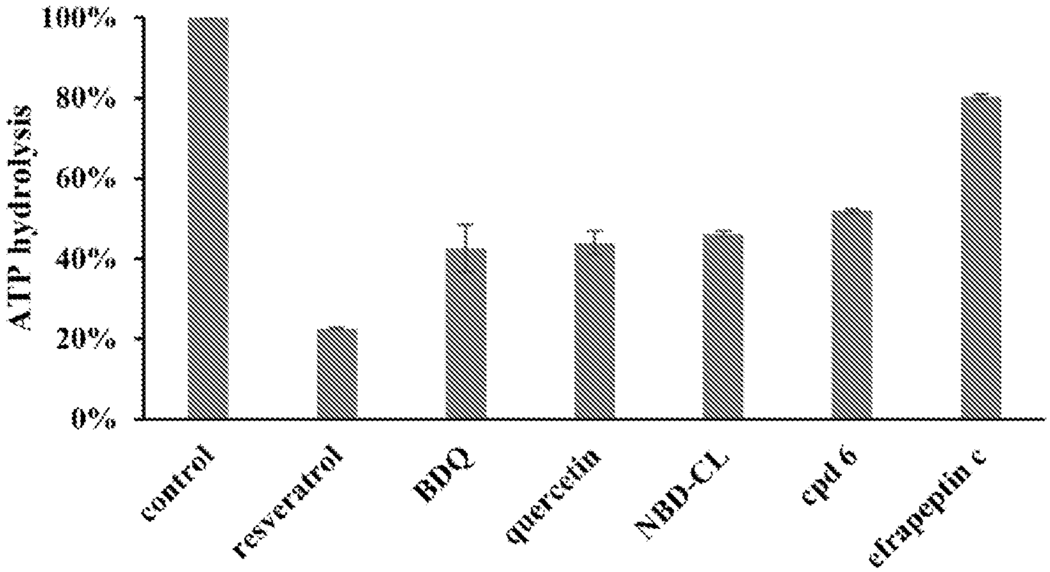
FIG. 3A shows the effect of ATPase inhibitors quercetin, NBD-Cl and efrapeptin c as compared to cpd 6 on the ATP hydrolysis activity of the mycobacterial F-ATP synthase of IMVs, thereby demonstrating its inhibitory traits in the ATP hydrolysis direction.

The new compound cpd 6 identified, blocks ATP synthesis of inverse membrane vesicles (IMV) of *Mycobacterium smegmatis* with an $IC_{50}$ value of about 300 nM which is comparable with the one reported recently for the drug BDQ using IMVs of *M. phlei* (20-25 nM, [1]). In addition, cpd 6 also inhibits ATP hydrolysis activity in a manner comparable to the known ATPase inhibitors quercetin, NBD-Cl, and even better then F-ATP synthase inhibitor efrapeptine (FIG. 3A). The dual effect of ATP synthesis and ATP hydrolysis inhibition by cpd 6 indicates that cpd 6 interacts with the soluble $F_1$ part of the enzyme in contrast to the lipophilic BDQ, which mainly interacts with the hydrophobic and membrane-embedded c subunit, paving the way for a more soluble compound.

Figure 3B:
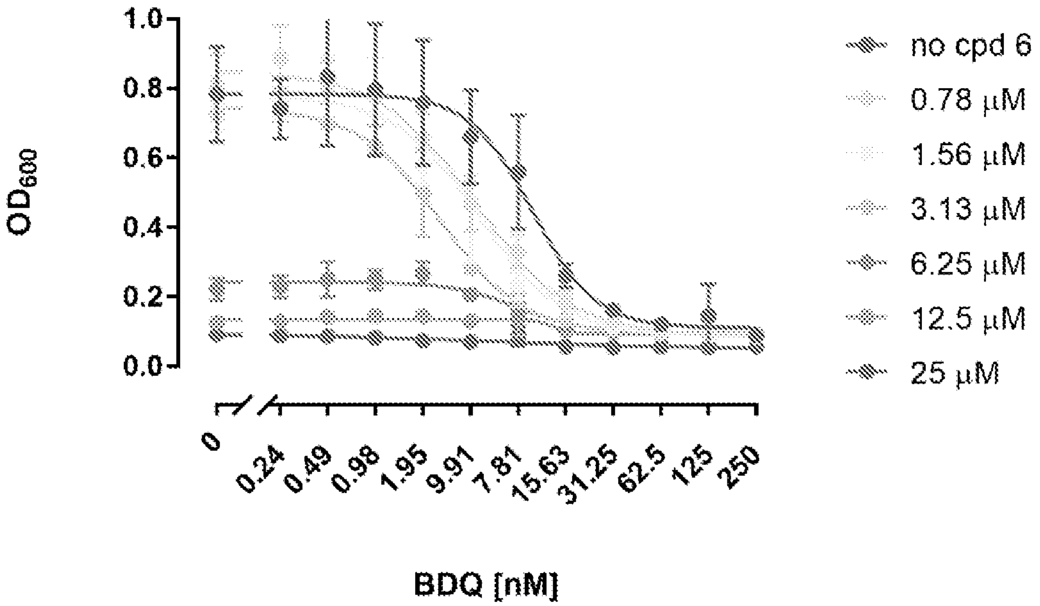
FIG. 3B reveals the synergistic effect of the TB drug BDQ and cpd 6 on ATP synthesis of IMVs of *M. smegmatis*. A combination of different concentrations of BDQ and cpd 6 (0-250 nM and in a range of 0-25 μM, respectively) was achieved by carrying out two subsequent serial dilutions in the 96 well plate containing 100 μl of 7H9 media. Suspension of *M. smegmatis* $mc^2$ 155 in logarithmic growth phase was added to obtain starting $OD_{600}$=0.05 in 200 μl. Plates were incubated 24 h in 37° C.
Figure 3C:
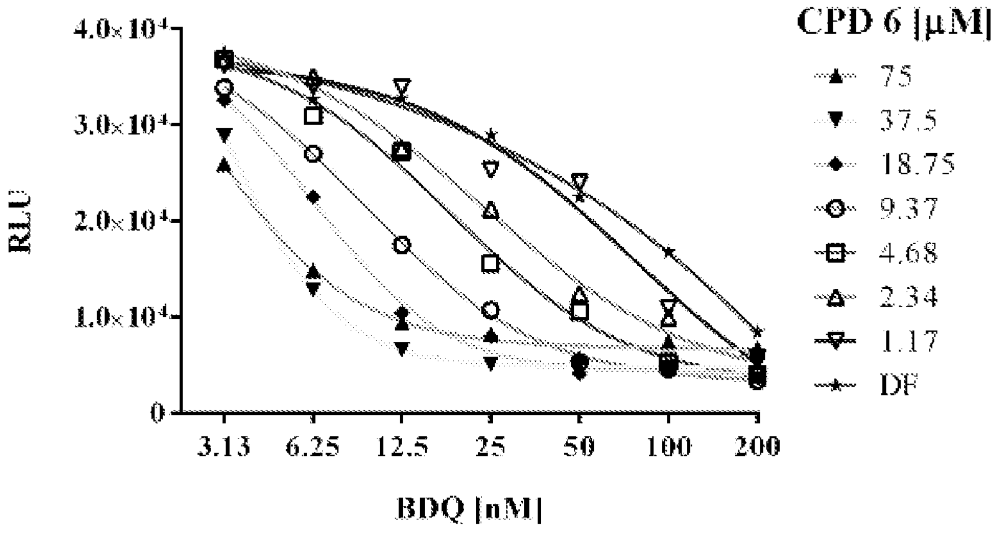
FIG. 3C shows the whole cell ATP synthesis assay with *M. bovis* BCG in the presence of BDQ and cpd 6. BDQ alone at 200 nM inhibits ATP synthesis from $3.7\times10^4$ RLU to $8\times10^3$ RLU. Interestingly, in the presence of 37.5 μM of cpd 6, only 12.5 nM of BDQ is needed to achieve similar inhibition ($6.5\times10^3$ RLU)
Figure 3D:
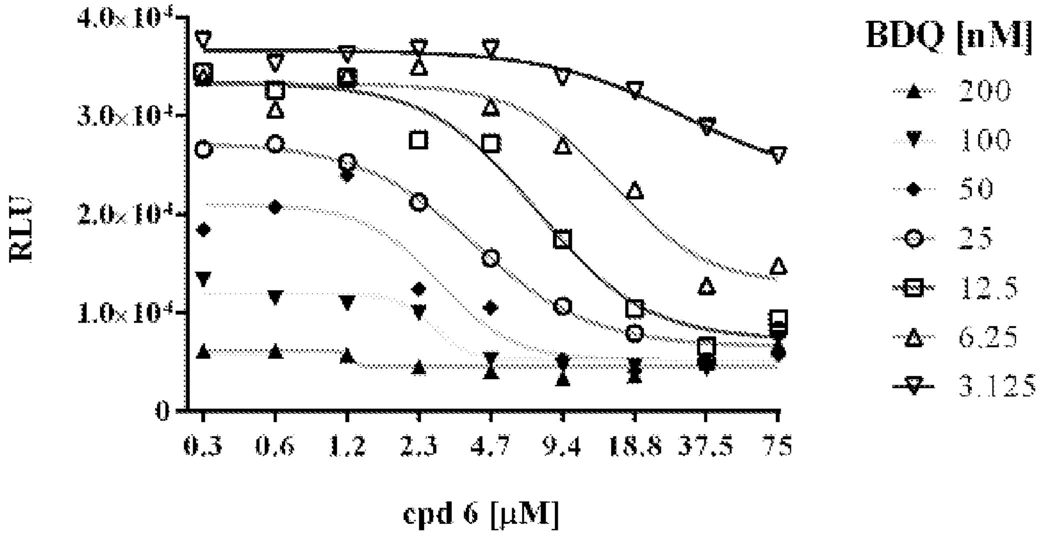
FIG. 3D shows the reduction of the $IC_{50}$ value of BDQ from 42 nM for BDQ alone to 2.36 nM when used in combination with cpd 6.
Figure 3E:
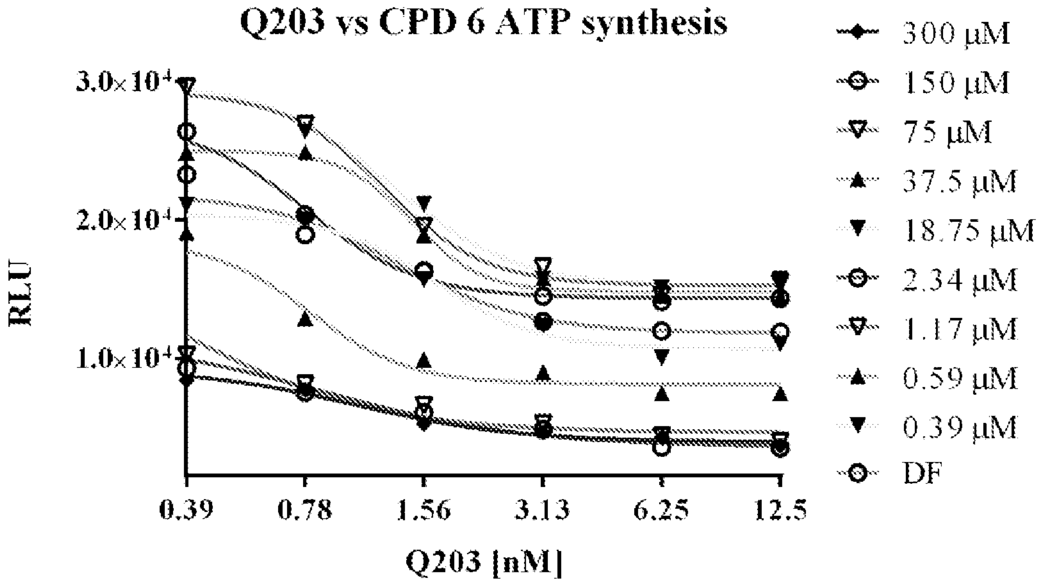
FIG. 3E shows the additive effect of Q203 in the presence of cpd 6.

A major step forward is the observation that cpd 6 shows an additive effect when incubated with BDQ (FIG. 3B) and Q203. The additive effect of cpd 6 and BDQ (FIG. 3C and 3D) or Q203 (FIG. 3E) goes along with a significant reduction of ATP synthesis. Studies of cpd 6 with BDQ and Q203 on the oxygen consumption rate reveal that extracellular oxygen consumption is inhibited at a concentration of about 500 nM BDQ and cpd 6 at approximately 400 μM. However, when used in combination, only 50 nm of BDQ and 40 μM of cpd 6 are needed to reach similar inhibition. A similar additive effect is observed for the combination of cpd 6 and Q203, whereby a complete inhibition with 100 nM of Q203 and 40 μM of cpd 6 is achieved. This opens a new avenue for a highly efficient multi-drug combination.

Figure 4:
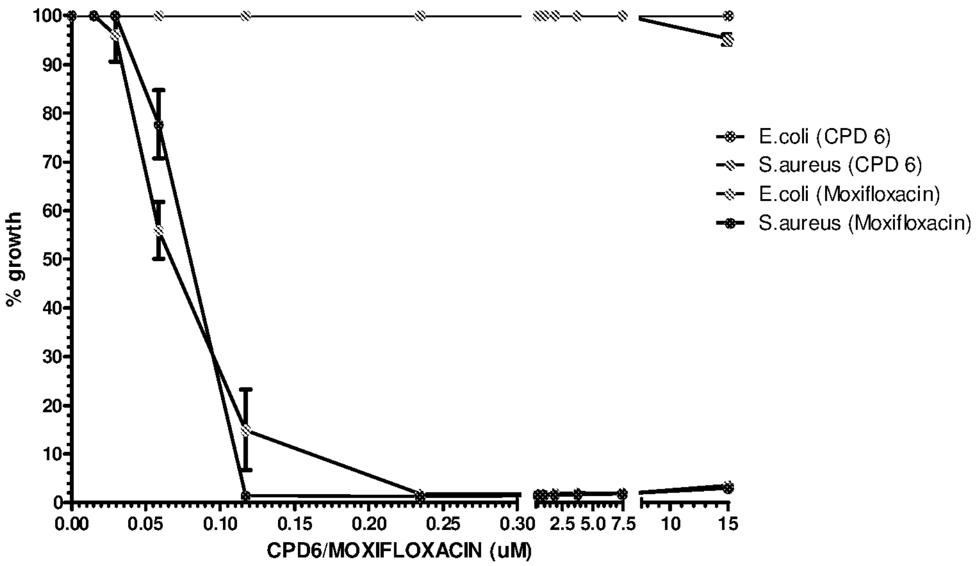
FIG. 4 shows a screen of cpd 6 against the human microbiome representatives, *Staphylococcus aureus* and *Escherichia coli*. The compound, Moxiflocaxin, was used as a control.
Figure 5:
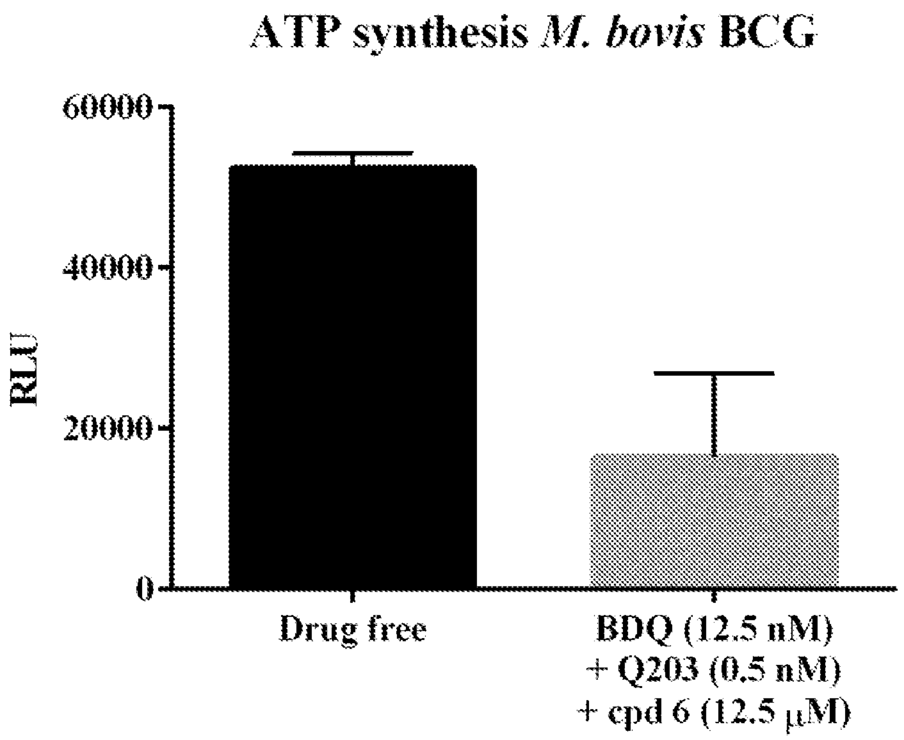
FIG. 5 shows the effect of whole cell ATP synthesis inhibition in *M. bovis* BCG using a combination of BDQ at 12.5 nM, Q203 at 0.5 nM and cpd6 at 12.5 μM against a control that does not contain a compound of the present invention or any drug (i.e. drug free)

A screen of cpd 6 against the Gram-positive bacterium, *Staphylococcus aureus*, and a representative Gram-negative bacterium, *Escherichia coli*, as representatives of the human microbiome, confirmed the specificity of cpd 6 for Tuberculosis as well as that the compound does not affect the human microbiome (FIG. 4). This is in line with the very good mouse liver microsome stability of the compound, with a T½-value of 47.5 min, a $Cl_{int}$-values of 14.6 μl/min/mg protein, and a T½ w/o NADPH value of 68.0 min.

Finally, a synergistic effect of cpd 6 with BDQ and Q203, respectively, in a multi-drug combination was tested.

In Vivo Testing of Compounds

All in vivo experiments are carried out as described in Negatu et al. (2017) Antimicrobial Agents and Chemotherapy, doi:10.1128/AAC.01571-17

Animals and ethics assurance. Mouse studies are carried out in accordance with the Guide for the Care and Use of Laboratory Animals of the National Institutes of Health, with approval from the Institutional Animal Care and Use Committee of the New Jersey Medical School, Newark (CD-1 mice), National University of Singapore's Institutional Animal Care and Use Committee (BALB/c mice). All animals are maintained under specific pathogen-free conditions and fed water and chow ad libitum, and all efforts are made to minimize suffering or discomfort. Studies in *M. tuberculosis* infected animals are performed in biosafety level 3 facilities approved for the containment of *M. tuberculosis.*

Pharmacokinetic (PK) analyses. PK studies are performed in uninfected CD-1 mice after single dose compounds (such as Cpd 6 and its analogs) or compositions thereof at 5 mg/kg via the intravenous (i.v.) route and 100 mg/kg via the oral route (p.o.), as described in Lakshminarayan, S. B., Huat, T. B., Ho, P. C., Manjunatha, U. H., Dartois, V, Dick, T. Rao, S. P. S. (2015) Comprehensive physicochemical, pharmacokinetic and activity profiling of anti-TB agents *J. Antimicrob. Chemoth.* 70, 857-867. The i.v. formulation may be for instance 5% dimethylacetamide (DMA)/95% of a 4% Cremophor solution. The p.o. formulation may be either 50% PEG400 (polyethylene glycol)/50% D5W (dextrose 5% in sterile water) to generate a solution, or 0.5% CMC (carboxymethylcellulose) and 0.5% Tween 80 in water to generate a suspension. In the i.v. arm, blood was collected in $K_2$EDTA coated tubes pre-dose, and at 1 min, 15 min, 1 h, 3 h, 5 h, 8 h and 24 h post dose. In the p.o. arms, blood was collected pre-dose and at 15 min, 30 min, 1 h, 3 h, 5 h, 8 h and 24 h post dose. Plasma was obtained by centrifugation for 10 min at 5,000 rpm and stored at −80° C. until analyzed. Drug concentrations (includes concentrations of compounds or compositions thereof) are measured as described below. The PK parameters (area under the curve [$AUC_{0-t}$ and $AUC_{0-24}$], peak plasma concentration [$C_{max}$], and half-life [$t_{1/2}$]) are calculated from mean concentrations using Microsoft Excel (Office 2010; Microsoft Corp., Redmond, Wash.). AUCs are calculated using the linear trapezoidal rule. Half-life and elimination rate constants are calculated by linear regression using semi-logarithmic concentration versus time data.

Analytical Methods. Neat 1 mg/ml DMSO stocks of drug are first serially diluted in 50/50 Acetonitrile/Water and subsequently serially diluted in drug free CD1 mouse plasma ($K_2$EDTA, Bioreclamation IVT, NY) to create standard curves and quality control (QC) spiking solutions. Twenty (20) μl of standards, QC samples, control plasma, and study samples were extracted by adding 200 μl of Acetonitrile/Methanol 50/50 protein precipitation solvent containing the internal standard (10 ng/ml Verapamil). Extracts were vortexed for 5 min and centrifuged at 4,000 RPM for 5 min. One hundred (100) μl of supernatant was transferred for high pressure liquid chromatography coupled to tandem mass spectrometry (LC/MS-MS) analysis and diluted with 100 μl of Milli-Q deionized water.

LC/MS-MS quantitative analysis for drugs are performed on a AB Sciex Qtrap 6500+ triple-quadrupole mass spectrometer coupled to a Shimadzu 30ACMP HPLC system, and chromatography was performed on an Agilent Zorbax SB-C8 column (2.1×30 mm; particle size, 3.5 μm) using a reverse phase gradient elution. Milli-Q deionized water with 0.1% formic acid was used for the aqueous mobile phase and 0.1% formic acid in acetonitrile for the organic mobile phase. Multiple-reaction monitoring of parent/daughter transitions in electrospray positive-ionization mode was used to quantify all molecules. Sample analysis was accepted, if the concentrations of the quality control samples and standards were within 20% of the nominal concentration. Data processing was performed using Analyst software (version 1.6.2; Applied Biosystems Sciex).

Animal tolerability and efficacy experiments. Eight to ten week old female BALB/c mice were maintained in groups of 3 or 4 in individually ventilated cages under specific pathogen free conditions at the National University of Singapore biosafety level-3 core facility. Food and water were offered ad libitum. Test drugs may be formulated in equal volumes of polyethylene glycol 400 and 5% glucose and administered at a dose of 100 mg/kg in a volume of 200 μl by oral gavage. Acute toxicity was assessed by dosing groups of 3 mice on three consecutive days followed by a monitoring period of 7 days. Animals are subsequently euthanized by $CO_2$ to assess gross pathological changes. For in vivo efficacy determination of drug candidates, mice were infected with 100-200 CFU *M. tuberculosis* H37Rv using a full body inhalation exposure system (GlasCol). After 14 days, chemotherapy was initiated on 6 days per week for 4 weeks. Isoniazid (INH) at a dose of 25 mg/kg formulated in 0.25% methyl cellulose was served as control. Mice were euthanized at designated time points by $CO_2$. Bacterial burden of organs was determined by plating serial dilutions of organ homogenates onto Middlebrook 7H11 agar supplemented with 20 μg/ml ampicillin and 10 μg/ml cycloheximide. Colonies were counted after 3-4 weeks of incubation at 37° C.

It should be further appreciated by the person skilled in the art that variations and combinations of features described above, not being alternatives or substitutes, may be combined to form yet further embodiments falling within the intended scope of the invention.

The invention claimed is:

1. A composition comprising a compound having a structure represented by the following formula:

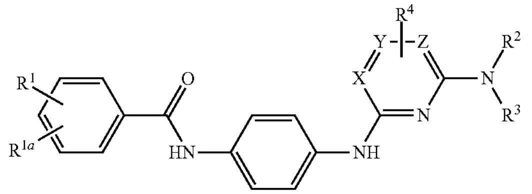

wherein $R^1$ and $R^{1a}$ are independently H, halogen, $C_1$-$C_4$ alkyl, $C_1$-$C_4$ alkoxy, OH;

$R^2$=H, $C_1$-$C_4$ alkyl, $C_1$-$C_4$ alkyl alcohol, $C_1$-$C_4$ alkoxy, —$CH_2$COOEt;

$R^3$=H, $C_1$-$C_4$ alkyl;

$R^4$=H, halogen, $C_1$-$C_4$ alkyl, $C_1$-$C_4$ alkoxy;

X, Y and Z are independently C or N, or a pharmaceutically acceptable salt thereof; and bedaquiline or 6-chloro-2-ethyl-N-[[4-[4-[4-(trifluoromethoxy)phenyl]piperidin-1-yl]phenyl]methyl]imidazo[1,2-a]pyridine-3-carboxamide (Q203), or a combination thereof.

2. A kit for treating tuberculosis, the kit comprising the composition of claim 1.

3. A method of treating tuberculosis in a patient, wherein the method comprises administering to a patient, a therapeutically effective amount of the composition of claim 1.

4. The composition according to claim 1, wherein $R^2$ of the compound is ethyl and $R^3$ of the compound is H.

5. The composition according to claim 1, wherein X of the compound is N, Y and Z of the compound are C.

6. The composition according to claim 1, wherein $R^1$ of the compound is selected from the group consisting of 3-Br, 3-F, 3-OH, 4-Me and 4-OMe.

7. The composition according to claim 1, wherein $R^{1a}$ of the compound is selected from the group consisting of 5-Br, 5-F and 5-OH.

8. The composition according to claim 1, wherein $R^{1a}$ of the compound is hydrogen.

9. The composition according to claim 1, wherein $R^2$ of the compound is selected from the group consisting of $—CH_2CH_2OH$, $—CH_2COOEt$, methyl, ethyl and isopropyl.

10. The composition according to claim 1, wherein the compound is selected from the group of one of the following structures:

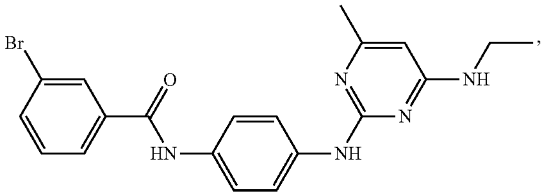

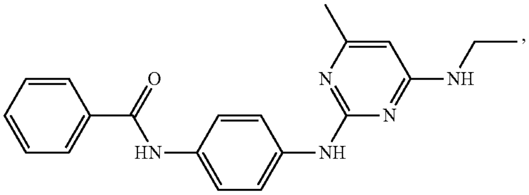

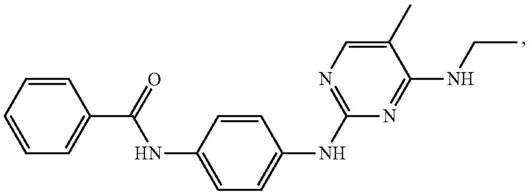

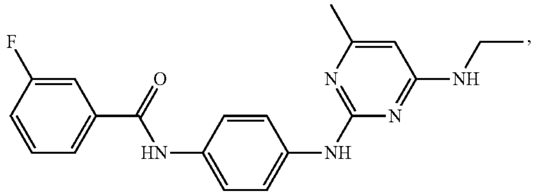

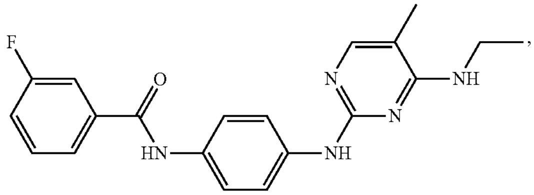

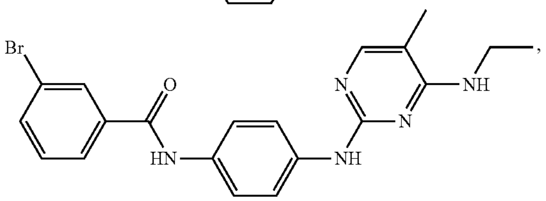

-continued

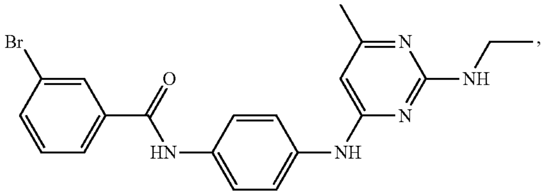

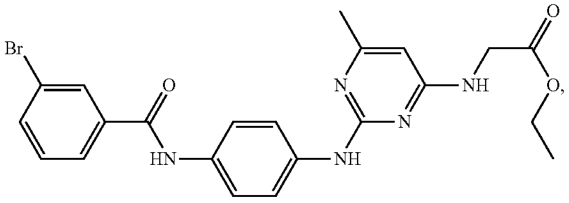

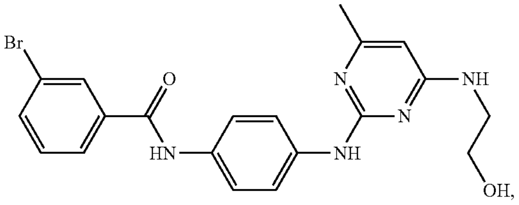

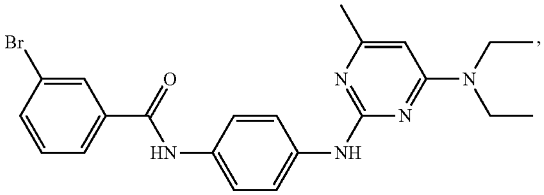

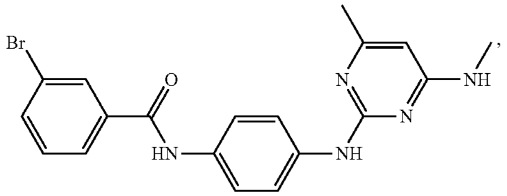

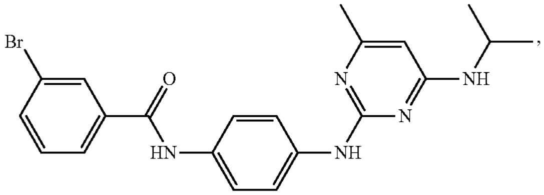

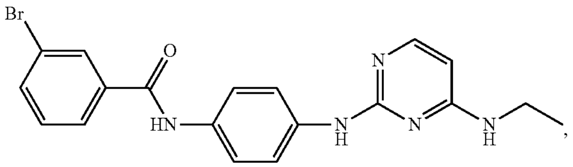

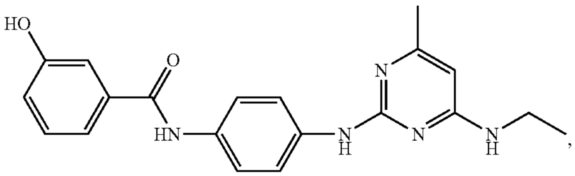

-continued
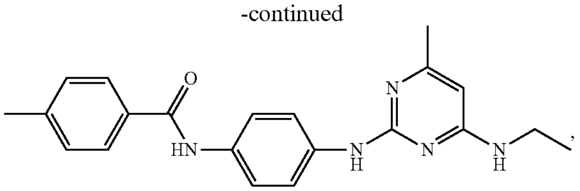
and
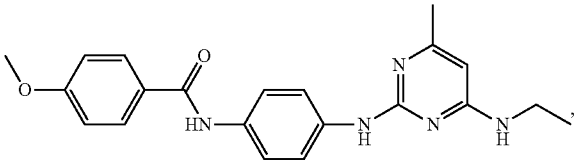
or a pharmaceutically acceptable salt thereof.
* * * * *